United States Patent [19]
Yadan et al.

[11] Patent Number: 6,056,965
[45] Date of Patent: May 2, 2000

[54] 2-MERCAPTO-IMIDAZOLE DERIVATIVES SUBSTITUTED IN POSITION 4 (OR 5) AS ANTIOXIDIZING AGENTS, METHOD OF PREPARATION AND APPLICATIONS IN THE PHARMACEUTICAL, COSMETIC OR FOOD INDUSTRIES

[75] Inventors: Jean-Claude Y. Yadan, Paris; Jinzhu Xu, Ivry sur Seine; Marc E. Moutet, Bagneux; Jean R. Chaudiere, Saint Maur, all of France

[73] Assignee: Oxis Isle of Man, Limited, Portland, Oreg.

[21] Appl. No.: 08/929,069

[22] Filed: Sep. 15, 1997

Related U.S. Application Data

[63] Continuation of application No. 08/507,329, filed as application No. PCT/FR94/01514, Dec. 22, 1994, abandoned.

[30] Foreign Application Priority Data

Dec. 24, 1993 [FR] France ................................. 93 15637

[51] Int. Cl.[7] .......................... A61K 7/42; A61K 31/415; C07D 233/84; C07D 403/12
[52] U.S. Cl. .......................... 424/401; 424/59; 426/545; 252/402; 252/405; 514/252; 514/392; 544/370; 548/311.4; 548/316.4; 548/324.1; 548/324.5; 548/325.1
[58] Field of Search .............................. 548/311.4, 316.4, 548/324.1, 324.5, 325.1; 514/392, 252; 544/370; 424/59, 401; 426/545; 252/402, 405

[56] References Cited

U.S. PATENT DOCUMENTS 4,898,878  2/1990  Shapiro et al. ........................ 514/386

FOREIGN PATENT DOCUMENTS 1184710  2/1959  France .

OTHER PUBLICATIONS

CA 96:57746j Heme concentrate. Lindroos, p. 368, 1982.
CA 112:2268248 Photosensitive . . . production. Aoshima et al., p. 679, 1990.
CA 117: 107204f Assessment of . . . inhibitors. Lueoend et al., p. 421, 1992.
Archives of Biochemistry and Biophysics, vol. 288, No. 1, Jul. 1991, "The Antioxidant Action of Ergothioneine".
Biochemical Pharmacology, vol. 36, No. 9, May 1, 1987, "Antioxidant Properties of 2–Imdazolones and 2–Imidazolthiones".
R.A.F. Bullerwell, et al., "2–Mercaptoglyoxalines. Part VIII.* The Preparation of 2–Mercaptoglyoxalines from Glutamic Acid", 1953.
Archives of Biochemistry and Biophysics, vol. 281, No. 1, Aug. 15, 1990, "The Reduction of Ferryl Myoglobin by Ergothioneine: A Novel Function for Ergothioneine".

*Primary Examiner*—Joseph K. McKane
*Attorney, Agent, or Firm*—Jacobson, Price, Holman & Stern, PLLC

[57] ABSTRACT

The invention relates to 2-mercaptoimidazole derivatives substituted in the 4(or 5)-position.

These 2-mercaptoimidazole derivatives are of the general formula (I) below:

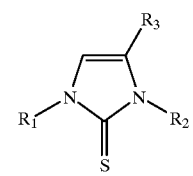

wherein:

$R_1$, $R_2$, $R_5$, $R_7$ and $R_8$ are hydrogen, a lower alkyl, an aralkyl or a substituted aralkyl, wherein at least one of $R_1$ and $R_2$ is hydrogen;

$R_3$ is $(CH_2)_nCOR_4$, $-(CH_2)_nN^+(R_5R_6R_7).X^-$ or $-CH_2CH(COR_4)N^+(R_5R_6R_7).X^-$;

$R_4$ is $OR_8$, $-NHR_5$, $-\alpha$-amino acid, $-NHCH_2CH_2SO_3^-.Y^+$, $-NHCH_2CH_2CO_2^-Y^+$, $-OCH_2CH_2N^+(CH_3)_3.X^-$;

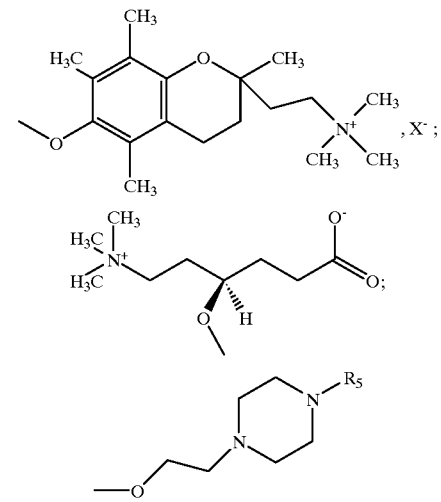

$n=1$ or $2$;

$X^{31}$ is an anion of an acid acceptable in cosmetics, pharmaceuticals or foodstuffs; and $Y^+$ is a cation of a base acceptable in cosmetics, pharmaceuticals or foodstuffs.

These compounds are valuable as antioxidants and as active principles of pharmaceutical, cosmetic or food compositions with antioxidant activity.

39 Claims, 4 Drawing Sheets

REDUCTION DE LA FERRYLMYOGLOBINE

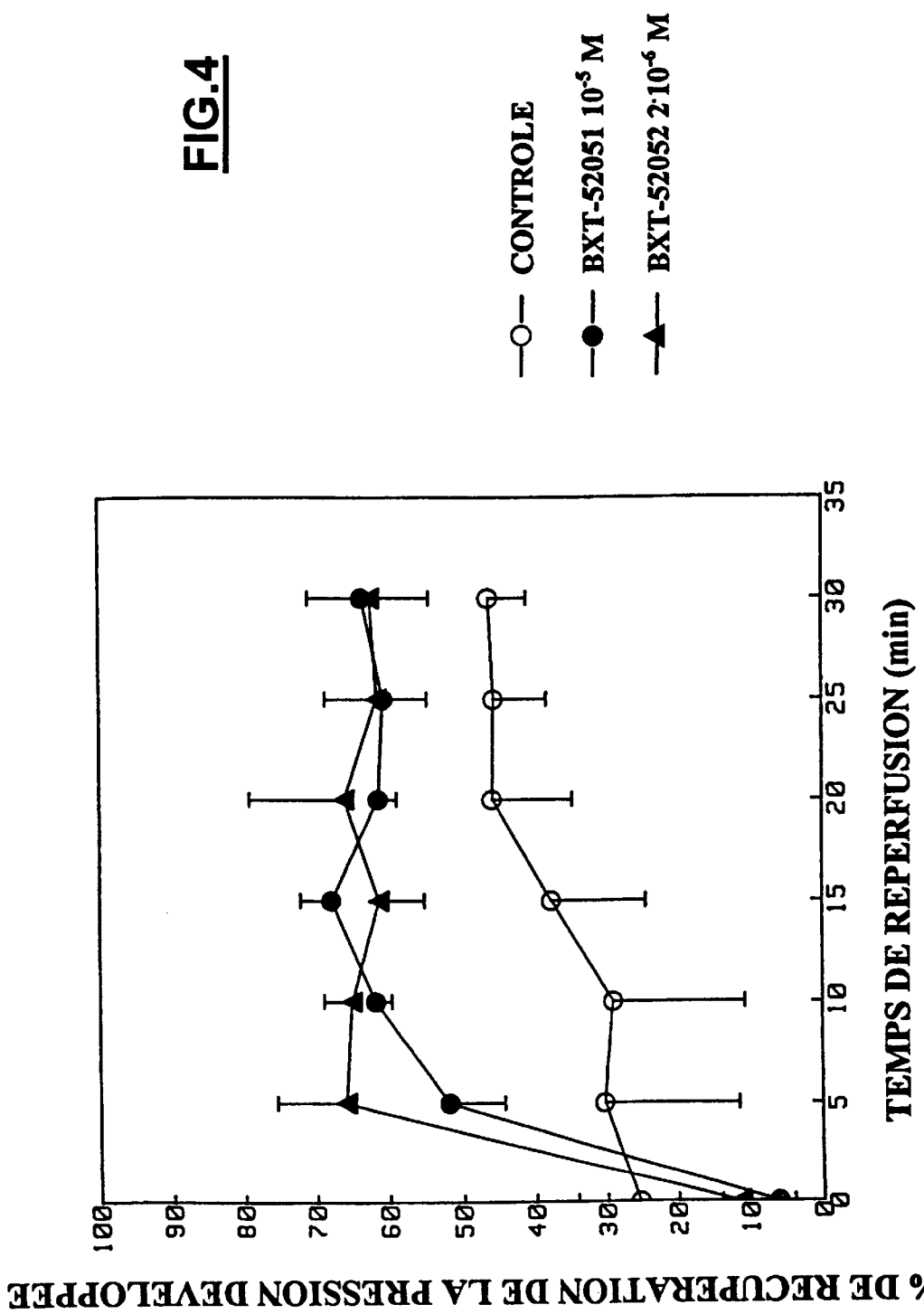

2-MERCAPTO-IMIDAZOLE DERIVATIVES SUBSTITUTED IN POSITION 4 (OR 5) AS ANTIOXIDIZING AGENTS, METHOD OF PREPARATION AND APPLICATIONS IN THE PHARMACEUTICAL, COSMETIC OR FOOD INDUSTRIES

This is a continuation of application Ser. No. 08/507,329, filed Aug. 23, 1995 which was abandoned upon the filing hereof;

This application is a continuation of Ser. No. 08/507,329 filed Aug. 23, 1995, now abandoned and a 371 of PCT/FR94/01514 filed Dec. 22, 1994.

The present invention relates to the use of 2-mercaptoimidazole derivatives substituted in the 4(or 5)-position as antioxidants, to the process for their preparation and to pharmaceutical, cosmetic or food compositions in which they are applied.

BACKGROUND OF THE INVENTION

Several 2-mercaptoimidazole derivatives substituted in the 4- or 5-position by a carbonyl-containing group (ketone, carboxyl or amide group) have been found to have antioxidant activity (see R. C. SMITH et al., Biochem. Pharmacol., (1987), 36, 9, pages 1457–1460) and anti-inflammatory activity (see S. MAEDA et al., Chem. Pharm. Bull., (1984), 32, pages 2536–2543).

The antioxidant properties of the novel 2-mercaptoimidazole derivatives forming the subject of the present invention are similar to that of L-(+)-ergothioneine, which forms part thereof.

L-(+)-Ergothioneine, a natural molecule with a 2-mercaptoimidazole structure, is biosynthesized by certain rye ergot fungi such as Claviceps purpurea (see C. TANRET, C.R. Acad. Sci., (1909), 149, pages 222–224). The chemical structure of L-(+)-ergothioneine is rare in the living world insofar as it is made up of a 2-mercaptoimidazole ring and a betaine (see G. G. SKELLERN in "Sulfur-containing drugs and related organic compounds: Chemistry, Biochemistry and Toxicology", L. A. DAMANI eds., Ellis Horwood Lim., (1989), vol. 1, part B, chap. 3, pages 49–89). Man is auxotrophic for ergothioneine, which he obtains exclusively through food. The physiological concentrations of ergothioneine vary between 0.1 and 2.0 mmolar in the erythrocytes, liver, kidney, seminal fluid and cataract-free lens. Although the biological role of ergothioneine is still uncertain, its antioxidant properties are well documented (see P. E. Hartman, Meth. Enzymol., (1990),186, pages 310–318, and D. AKANMU et al., Arch. Biochem. Biophys., (1991), 288, pages 10–16). Under physiological conditions (concentrations and pH), it reacts neither with hydrogen peroxide, $H_2O_2$, nor with the superoxide anion, $O_2^-$ (see D. AKANMU et al., Arch. Biochem. Biophys., (1991), 288, pages 10–16). By contrast, it reacts with the OH radicals produced by pulsed radiolysis (see M. ROUGEE et al., Photochem. Photobiol., (1988), 47, pages 485–489) or via the Fenton reaction (see D. AKANMU et al., Arch. Biochem. Biophys., (1991), 288, pages 10–16) with kinetics close to the maximum rate of diffusion; it reacts with hypochlorous acid, HOCl, thus preventing the inactivation of $\alpha_1$-antitrypsin (see D. AKANMU et al., Arch. Biochem. Biophys., (1991), 288, pages 10–16), and inhibits the photoproduction of singlet oxygen by quenching the excited states of photosensitizers such as rose bengal (see S. S. SPICER et al., Proc. Soc. Exp. Biol. Med., (1951), 77, page 418). Furthermore, like the majority of 2-mercaptoimidazole derivatives, ergothioneine forms very stable complexes with divalent metals such as $Cu^{++}$, $Hg^{++}$, $Zn^{++}$, $CO^{++}$ and $Ni^{++}$ (see D. P. HANLON, J. Med. Chem., (1971), 14, page 1084, and N. MOTOHASHI et al., Chem. Pharm. Bull., (1974), 22, pages 654–657). In contrast to numerous alkylmercaptans, RSH, such as glutathione or cysteine for example, ergothioneine does not stimulate the peroxidation of polyunsaturated fatty acids in the presence of metal salts ($Fe^{++}$) (see D. AKANMU et al., Arch. Biochem. Biophys., (1991), 288, pages 10–16), which is consistent with its properties as an inactivating chelating agent and with its predominantly thione structure. Another advantage of using antioxidants with a 2-mercaptoimidazole structure is their very high stability in aerated aqueous solution. In fact, since the tautomeric equilibrium of 2-mercaptoimidazole derivatives is totally displaced towards the thione form in solution (see E. BOJARSKA-OLEJNIK et al., Mag. Res. Chem., (1985), 23, pages 166–169), the sulfur atom of the 2-mercaptoimidazole ring does not react with the dissolved oxygen in practice. Yet another advantage of using antioxidants with a 2-mercaptoimidazole structure is that their disulfides are unstable in the presence of another mercaptan such as, for example, cysteine, cysteamine, glutathione or lipoic acid.

At micromolar concentrations, ergothioneine and some 2-mercaptoimidazole derivatives effectively inhibit the formation of methemoglobin from oxyhemoglobin incubated in the presence of sodium nitrite in vitro (see R. C. SMITH et al., Biochem. Pharmacol., (1987), 36, 9, pages 1457–1460, and R. A. MORTENSEN, Arch. Biochem. Biophys., (1953), 46, pages 241–243). It reduces the ferryl forms of the hemoproteins which are produced in the presence of hydrogen peroxide, $H_2O_2$, at physiological pH (see A. ARDUINI et al., Arch. Biochem. Biophys., (1990), 281, pages 41–43). The rapid reduction of ferrylmyoglobin ($Mb^{IV}$) could be an essential mechanism by which ergothioneine protects the muscular tissue in general, and the cardiac tissue in particular, during oxidative stress and in particular during postischemic reperfusion. In a postischemic reperfusion model of isolated rat heart, it has been shown that, after 15 min of ischemia, ergothioneine (100 $\mu$molar) limits the extent of cell necrosis evaluated by measurement of the lactate dehydrogenase activity of the effluent (see A. ARDUINI et al., Arch. Biochem. Biophys., (1990), 281, pages 41–43).

From the chemical point of view, 2-mercaptoimidazole derivatives have been obtained by two main routes, namely:
   generation of the 2-mercaptoimidazole ring either by reaction of an $\alpha$-amino ketone derivative with potassium thiocyanate (see S. MAEDA et al., Chem. Pharm. Bull., (1984), 32, pages 2536–2543, Y. ISOMURA et al., Chem. Pharm. Bull., (1984), 32, pages 152–165, and J. FERNANDEZ-BOLANOS et al., Anales de Quimica, (1974), 70, pages 94–95) or by reaction of an $\alpha$-halo ketone derivative with thiourea or a derivative thereof; and
   introduction of sulfur into the 2-position of an imidazole ring either by nucleophilic addition of a sulfur-containing derivative onto an electrophilic imidazole ring (see S. ITO, J. Org. Chem., (1985), 50, pages 3636–3638) or by electrophilic addition of sulfur onto a nucleophilic imidazole ring (see B. L. BENAC et al., Org. Synthesis, coll. vol. VII, pages 195–196).

SUMMARY OF THE INVENTION

The object of the present invention is to solve the new technical problem which consists in providing novel compounds which have a good antioxidant activity and preferably also a good cytoprotective activity, thereby making it possible to prepare a valuable active principle within the framework of pharmaceutical, cosmetic or food compositions.

A further object of the invention is to solve the abovementioned new technical problem by means of a solution which also provides a straightforward process for the preparation of these compounds with good yields.

The present invention solves the abovementioned technical problem for the first time, simultaneously, by means of a simple solution, with a relatively straightforward preparative process producing good yields and with a product of extremely high purity, in particular optical purity.

Indeed, the invention proposes a novel method of introducing sulfur into the 2-position of an imidazole ring, whose mechanism has something in common with a mechanism of the type Nucleophilic Addition—Ring Opening—Ring Closure (NARORC). The operating conditions of this novel method are sufficiently mild for the integrity of a chiral center, in particular that of the a-carbon of an amino acid, to be maintained.

Thus, according to a first feature, the present invention relates to the use of 2-mercaptoimidazole derivatives substituted in the 4(or 5)-position of general chemical formula (I) below:

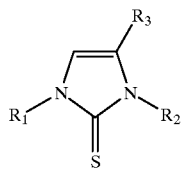

in which:

$R_1$ is hydrogen, a lower alkyl, an aralkyl group or a substituted aralkyl group;

$R_2$ is hydrogen, a lower alkyl, an aralkyl or a substituted aralkyl, knowing that at least one of $R_1$ and $R_2$ is hydrogen;

$R_3$ is $-(CH_2)_n COR_4$, $-(CH_2)_n N^+(R_5 R_6 R_7).X^-$ or $-CH_2CH(COR_4)N^+(R_5R_6R_7).X^-$;

$R_4$ is $-OR_8$, $-NHR_5$, -α-amino acid, preferably natural -α-amino acid, $-NHCH_2CH_2SO_3^{-}.Y^+$, $-NHCH_2CH_2CO_2^{-}.Y^+$, $-OCH_2CH_2N^+(CH_3)_3.X^-$,

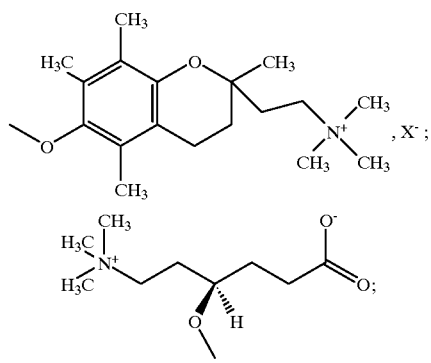

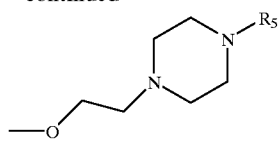

$R_5$ is hydrogen, a lower alkyl, an aralkyl or a substituted aralkyl;

$R_6$ is hydrogen, a lower alkyl, an aralkyl or a substituted aralkyl;

$R_7$ is hydrogen, a lower alkyl, an aralkyl or a substituted aralkyl;

$R_8$ is hydrogen, a lower alkyl, an aralkyl or a substituted aralkyl;

n=1 or 2;

$X^-$ is an anion of an acid acceptable in cosmetics, pharmaceuticals or foodstuffs; and $Y^+$ is a cation of a base acceptable in cosmetics, pharmaceuticals or foodstuffs, excluding L-ergothioneine, as antioxidants.

Within the framework of the description and the claims:

alkyl lower alkyl, alkoxy, lower alkoxy, acyl, amino acyl or carboxyl group is understood as meaning preferably linear or branched groups containing 1 to 6 carbon atoms;

the term substituted as applied to the aryl or aralkyl groups denotes that they are substituted on the aromatic moiety by one or more identical or different groups selected from lower alkyl, lower alkoxy, hydroxyl, amino and carboxyl, or by one or more hydrogen atoms;

when $R_8$ is a hydrogen atom, the invention also covers the addition salts of the abovementioned compounds of formula (I) with a base acceptable in pharmaceuticals, cosmetics or foodstuffs; and when $R_5$, $R_6$ or $R_7$ is a hydrogen atom, the invention also covers the addition salts of the abovementioned compounds of formula (I) with an acid acceptable in pharmaceuticals, cosmetics or foodstuffs.

Hydrochloric, hydrobromic, hydriodic, sulfuric, tartaric, methanesulfonic, trifluoromethanesulfonic and the like may be mentioned, without implying a limitation, among the acids acceptable in pharmaceuticals, cosmetics or foodstuffs.

Sodium and potassium hydroxides, alkali metal or alkaline-earth metal carbonates or organic bases such as triethylamine or arginine, and the like, may be mentioned, without implying a limitation, among the bases acceptable in pharmaceuticals, cosmetics and foodstuffs which can be added, if appropriate, to the compounds in which $R_8$ is a hydrogen atom in order to give a salt.

In one advantageous embodiment, the present invention relates to the use of the abovementioned compounds of formula (I) for the manufacture of a pharmaceutical composition with antioxidant activity, in particular for treating a pathological condition involving oxidative stress associated with an overproduction of oxidizing free radicals and/or with an intracellular decompartmentalization of the pool of certain transition metals such as iron, copper or manganese.

In another advantageous embodiment, the present invention relates to the use of the abovementioned compounds of formula (I) for the manufacture of a pharmaceutical composition for preventing the tissue degeneration induced by ischemia or postischemic reperfusion, and in particular for preventing myocardial infarction, and for preventing the postischemic cardiac arrhythmia which is the source of ventricular fibrillation; for preventing the tissue degeneration, such as edema, necrosis and fibrosis, associated with an overproduction of free radicals, comprising especially the treatment of intoxication by xenobiotics such as, for example, paraquat, diquat, anthracyclines or nitrofurans, or the pathological conditions associated with oxidative stress in erythrocytes, in particular sickle cell anemia, thalassemia, glucose-6-phosphate dehydrogenase deficiency diseases and malaria; for protecting against irradiation by ionizing X-rays or gamma rays as well as UV rays; or for protecting, in preserving media, grafts such as, for example, the heart, liver, kidney or lung, in organ transplants.

In another advantageous embodiment, the present invention relates to the use of the compounds of formula (I) given above for the manufacture of cosmetic compositions with antioxidant activity, in particular for protecting against UV rays.

In another advantageous embodiment, the present invention relates to the use of the compounds of formula (I) given above for the manufacture of food compositions with antioxidant activity.

In another advantageous embodiment, the 2-mercaptoimidazole derivative of formula (I) given above is present in an amount of between 0.1 and 5% by weight, preferably of between 0.1 and 1% by weight, based on the total weight of the final composition.

In another advantageous embodiment, the present invention relates to the use of the composition in the form of a unit dose which can comprise from 1 to 500 mg of 2-mercaptoimidazole derivative, if appropriate in a pharmaceutically acceptable excipient, vehicle or carrier.

According to a second feature, the present invention further provides a pharmaceutical, cosmetic or food composition, in particular with antioxidant activity, which comprises, as the active ingredient, at least one 2-mercaptoimidazole compound of general formula (1) below:

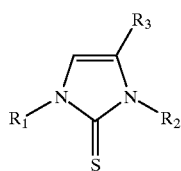

in which:

$R_1$ is hydrogen, a lower alkyl, an aralkyl group or a substituted aralkyl group;

$R_2$ is hydrogen, a lower alkyl, an aralkyl or a substituted aralkyl, knowing that at least one of $R_1$ and $R_2$ is hydrogen;

$R_3$ is $-(CH_2)_nCOR_4$, $-(CH_2)_nN^+(R_5R_6R_7).X^-$ or $-CH_2CH(COR_4)N^+(R_5R_6R_7).X^-$;

$R_4$ is $-OR_8$, $-NHR_5$, -α-amino acid, preferably natural -α-amino acid,
$-NHCH_2CH_2SO_3^-.Y^+$, $-NHCH_2CH_2CO_2^-.Y^+$,
$-OCH_2CH_2N^+(CH_3)_3.X^-$

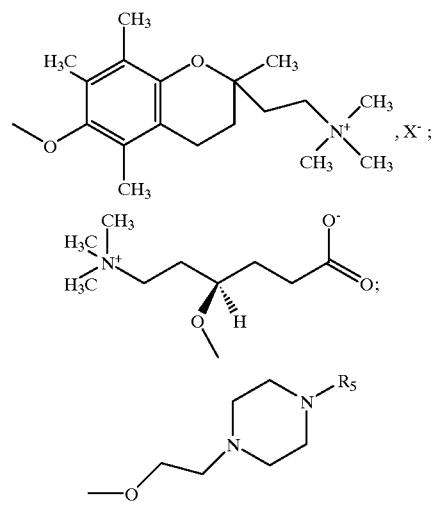

$R_5$ is hydrogen, a lower alkyl, an aralkyl or a substituted aralkyl;

$R_6$ is hydrogen, a lower alkyl, an aralkyl or a substituted aralkyl;

$R_7$ is hydrogen, a lower alkyl, an aralkyl or a substituted aralkyl;

$R_8$ is hydrogen, a lower alkyl, an aralkyl or a substituted aralkyl;

n=1 or 2;

$X^-$ is an anion of an acid acceptable in cosmetics, pharmaceuticals or foodstuffs; and $Y^+$ is a cation of a base acceptable in cosmetics, pharmaceuticals or foodstuffs, excluding L-ergothioneine if appropriate in an excipient, carrier or vehicle acceptable in pharmaceuticals, cosmetics or foodstuffs.

Other particular embodiments of this composition are clearly apparent from the foregoing description and will also be clearly apparent to those skilled in the art from the description which follows, including the Examples.

According to a third feature, the present invention also covers a process for the manufacture of a 2-mercaptoimidazole derivative of general formula (I) below:

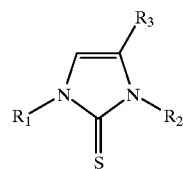

in which:

$R_1$ is hydrogen, a lower alkyl, an aralkyl group or a substituted aralkyl group;

$R_2$ is hydrogen, a lower alkyl, an aralkyl or a substituted aralkyl, knowing that at least one of $R_1$ and $R_2$ is hydrogen;

$R_3$ is $-(CH_2)_nCOR_4$, $-(CH_2)_nN^+(R_5R_6R_7).X^-$ or $-CH_2CH(COR_4)N^+(R_5R_6R7).X^-$;

$R_4$ is $-OR_8$, $-NHR_5$, -α-amino acid, preferably natural -α-amino acid,
$-NHCH_2CH_2SO_3^-.Y^+$, $-NHCH_2CH_2CO_2^-.Y^+$,
$-OCH_2CH_2N+(CH_2)_2.X^-$,

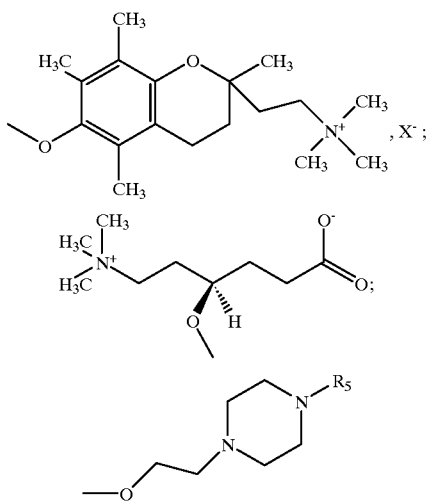

$R_5$ is hydrogen, a lower alkyl, an aralkyl or a substituted aralkyl;
$R_6$ is hydrogen, a lower alkyl, an aralkyl or a substituted aralkyl;
$R_7$ is hydrogen, a lower alkyl, an aralkyl or a substituted aralkyl;
$R_8$ is hydrogen, a lower alkyl, an aralkyl or a substituted aralkyl;
n=1 or 2;
$X^-$ is an anion of an acid acceptable in cosmetics, pharmaceuticals or foodstuffs; and
$Y^+$ is a cation of a base acceptable in cosmetics, pharmaceuticals or foodstuffs, which comprises the following essential steps:
a) preparing or using an optionally protected imidazole derivative substituted in the 4(or 5)-position, and optically active if necessary;
b) treating this imidazole derivative with an alkyl, alkenyl or aryl halothioxoformate in a basic medium in a polar solvent; and then
c) depending on the particular case:
  i—for the preparation of compounds of formula (I) given above in which $R_3$ is as defined above, with the proviso that $R_5$, $R_6$ and $R_7$ are not all simultaneously other than hydrogen, hydrolyzing in a basic medium or in an acid medium in the presence of a carbonium ion scavenger; or
  ii—for the preparation of the compounds of formula (I) given above in which $R_5$, $R_6$ and $R_7$ are simultaneously other than hydrogen, protecting the sulfur-containing substituent and then converting the protected compound to a trialkylammonium compound and hydrolyzing in a basic medium or in an acid medium in the presence of a carbonium ion scavenger, preferably in an acid medium in the presence of a carbonium ion scavenger if it is desired to preserve the optical activity of an already existing chiral center.

In one advantageous embodiment of this process, the abovementioned carbonium ion scavenger in said process is a mercaptan, preferably an alkyl or aryl mercaptan and better still β-mercaptopropanoic acid.

In yet another advantageous embodiment, the abovementioned base is preferably sodium bicarbonate, an amine or an alkylamine such as, for example, diethylamine or triethylamine.

In another particular embodiment, the abovementioned polar solvent may be chosen from an ether solvent such as, for example, ethyl ether or tetrahydrofuran, or an alcohol such as, for example, methanol.

In yet another advantageous embodiment, the abovementioned basic hydrolysis is performed with an inorganic base such as, for example, sodium hydroxide or lithium hydroxide, or an organic base such as an amine or an alkylamine, in particular diethylamine or triethylamine, especially in solution in a polar solvent preferably comprising a water/alcohol, in particular methanol, mixture.

In another advantageous embodiment, the abovementioned acid hydrolysis is performed with a concentrated solution of a strong acid at a pH below 2, in the presence of a carbonium ion scavenger, in particular a mercaptan, preferably in large excess.

In another advantageous embodiment, the abovementioned sulfur-containing substituents are protected by means of a haloformate, preferably an alkyl or phenyl haloformate, for example ethyl or phenyl chloroformate; the conversion to a trialkylammonium compound is effected by means of an alkylating agent such as, for example, an alkyl halide or sulfate, in particular methyl iodide or dimethyl sulfate.

According to another particularly advantageous characteristic, an optically active final derivative is prepared using an optically active starting compound, which is hydrolyzed with a concentrated acid solution at a pH below 2 and in the presence of a carbonium ion scavenger, preferably a mercaptan, in large excess.

According to a fourth feature, the present invention provides novel 2-mercaptoimidazole derivatives substituted in the 4(or 5)-position of general formula (I) below:

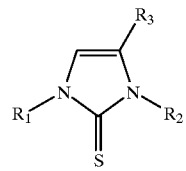

in which:
$R_1$, $R_2$ and $R_3$ are as defined in claim 1 and n=2, it being understood that:
a) if $R_4$=—$OR_8$, then $R_1$ and $R_2$ cannot simultaneously be hydrogen;
b) if $R_1$ and $R_2$ are: simultaneously hydrogen and if $R_4$=—$OR_8$, then $R_5$, $R_6$ and $R_7$ cannot simultaneously be hydrogen;
c) if $R_3$=—$CH_2CH(COR_4)N^+(R_5R_6R_7).X^-$ and $R_4$=OH or OMe, then $R_5$, $R_6$ and $R_7$ cannot simultaneously be a methyl group, and
d) if $R_3$=—$(CH_2)_2N^+(R_5R_6R_7).X^-$, then $R_5$, $R_6$ and $R_7$ cannot simultaneously be hydrogen.

As already stated, the 2-mercaptoimidazole compounds substituted in the 4(or 5)-position of formula (I) given above represent valuable antioxidants.

Within this framework, they represent valuable active agents in a therapeutic application.

In general terms, the therapeutic applications of the compounds of general structure I include any pathological conditions involving oxidative stress associated with an overproduction of oxidizing free radicals and/or with an intracellular decompartmentalization of the pool of certain transition metals such as, for example, iron, copper or manganese.

More specifically, said applications include:

the prevention of the tissue degeneration induced by ischemia and/or postischemic reperfusion, and in particular the prevention of myocardial infarction, and the prevention of the postischemic cardiac arrhythmia which is the source of ventricular fibrillation;

the prevention of the tissue degeneration, such as edema, necrosis and fibrosis, associated with an overproduction of free radicals: this application includes especially the treatment of intoxication by xenobiotics such as, for example, paraquat, diquat, anthracyclines or nitrofurans;

the pathological conditions associated with oxidative stress in erythrocytes, in particular sickle cell anemia, thalassemia, glucose-6-phosphate dehydrogenase deficiency diseases and malaria;

protection against irradiation by ionizing X-rays or gamma rays as well as UV rays; and the protection, in preserving media, of grafts such as, for example, the heart, liver, kidney or lung, in organ transplants.

In these therapeutic applications, the derivatives of the invention of formula (I) given above will advantageously be presented in the form of a unit dose which can comprise from 1 to 500 mg of 2-mercaptoimidazole derivatives, if appropriate in a pharmaceutically acceptable excipient, vehicle or carrier.

Such pharmaceutically acceptable excipients, vehicles or carriers are well known to those skilled in the art and are not therefore described in detail here.

The antioxidant and therapeutic or pharmacological activities of the 2-mercaptoimidazole derivatives substituted in the 4(or 5)-position of formula (I) given above were demonstrated by means of safe and reliable tests well recognized by those skilled in the art, which comprise:

a) the ferrylmyoglobin reduction test;

b) the test for preventing the inactivation of glutathione peroxidase by hypochlorous acid;

c) the test for preventing the inactivation of glucose-6-phosphate dehydrogenase by the system Cu(II)/ascorbate/$O_2$;

d) the test for preventing the degradation of DNA by the system Fe(II)-citrate/$H_2O_2$/ascorbate; and e) the test for inhibiting the cardiac necrosis induced by a period of ischemia-reperfusion.

f) the test for protecting the mechanical (ventricular) function of a heart subjected to a period of ischemia.

In view of these antioxidant and therapeutic/pharmacological activities, the 2-mercaptoimidazole derivatives substituted in the 4(or 5)-position of general formula (I) given above allow the therapeutic applications listed above to be carried out, and more particularly:

the prevention of the tissue degeneration induced by ischemia and/or postischemic reperfusion, and in particular the prevention of myocardial infarction, and the prevention of the postischemic cardiac arrhythmia which is the source of ventricular fibrillation;

the prevention of the tissue degeneration, such as edema, necrosis and fibrosis, associated with an overproduction of free radicals: this application includes especially the treatment of intoxication by xenobiotics such as, for example, paraquat, diquat, anthracyclines or nitrofurans;

the pathological conditions associated with oxidative stress in erythrocytes, in particular sickle cell anemia, thalassemia, glucose-6-phosphate dehydrogenase deficiency diseases and malaria;

the protection against irradiation by ionizing X-rays or gamma rays as well as UV rays; and the protection, in preserving media, of grafts such as, for example, the heart, liver, kidney or lung, in organ transplants.

Other objects, characteristics and advantages of the invention will become clearly apparent from the following explanatory description referring to various non-limiting Examples, which are given simply by way of illustration and cannot therefore in any way limit the scope of the invention. All the percentages are given by weight in the Examples, unless otherwise indicated.

I=end of stabilization;

II=5 min after reperfusion;

III=15 min after reperfusion.

For the compound BXT 52021, the periods IA, IIA, IIIA and IVA respectively denote:

IA=end of stabilization;

IIA=12 min after perfusion with the compound BXT 52021 (2 $\mu$M);

IIIA=5 min after postischemic reperfusion with BXT 52021 (2 $\mu$M);

IVA=15 min after postischemic reperfusion with BXT 52021 (2 $\mu$M).

Figure 3:
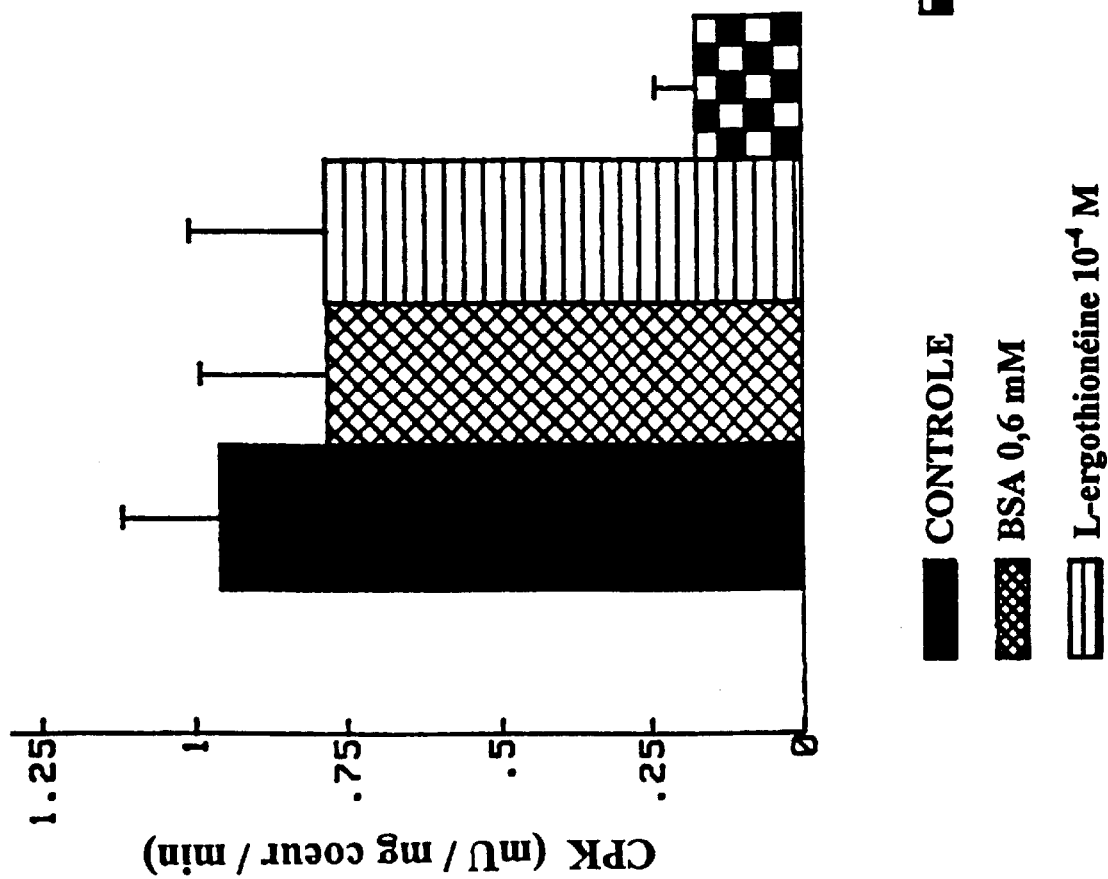

FIG. 3 represents the effect of one compound of the invention, BXT 52053, on the release of creatin phosphokinase (CPK) in an isolated and perfused rat heart subjected to an ischemia-reperfusion, with, on the ordinate, the total quantity of CPK released (expressed in milliunits of enzyme activity per milligram of heart and per minute). The effect of the compound BXT 52053 is, in addition, compared with that of albumin (BSA) and L-(+)-ergothioneine;

FIG. 4 represents the effects of the compounds of the invention, BXT 52051 and BXT 52052, on the percentage recovery of the pressure developed during the reperfusion of an isolated rat heart subjected to a period of ischemia, with, on the abscissa, the reperfusion time expressed in minutes and, on the ordinate, the percentage recovery of the developed pressure.

EXPERIMENTAL SECTION

All the reactions were performed under an inert nitrogen atmosphere, unless otherwise indicated.

The mass spectra were recorded on a Nermag R10-10B instrument. The ionization mode used is either electron impact (EI) at 70 electron volts, or chemical ionization (CI) in ammonia, or fast atom bombardment (FAB) on a glycerol matrix.

The $^1$H and $^{13}$C NMR spectra were recorded on a Varian Gemini-200 instrument. The chemical shifts are expressed in ppm relative to tetramethylsilane. The multiplicities are expressed as follows: "s" for singlet, "bs" for broad singlet, "d" for doublet, "t" for triplet, "q" for quadruplet and "m" for multiplet.

The melting points (m.p. ° C.) were recorded on a Gallenkamp instrument and are given uncorrected.

The optical rotation ($\alpha$D) was measured on a Perkin Elmer 241 instrument at 25° C. on the sodium D line.

The purifications by column liquid chromatography were effected with Merck® Si60 $F_{254}$ silica or Merck® microcrystalline cellulose, as appropriate.

I/EXAMPLES OF THE SYNTHESIS OF COMPOUNDS OF GENERAL FORMULA I

Example 1

Preparation of ethyl 3-(2'-mercaptoimidazol-4'-yl) propanoate: BXT 52021

A/Preparation of the ethyl ester of urocanic acid

Urocanic acid (Aldrich; 5.52 g; 40 mmol) is suspended in 100 ml of absolute ethanol. Para-toluenesulfonic acid monohydrate (Janssen; 8.36 g; 44 mmol) is added. The mixture is refluxed for 12 h. The solvent is evaporated off under reduced pressure. The residue is taken up in 50 ml of a saturated aqueous solution of $NaHCO_3$ and 75 ml of ethyl acetate. The organic phase is separated off and washed with the same volume of a saturated aqueous solution of NaCl (2×50 ml). After the organic phase has been dried over $MgSO_4$ and filtered, the solvent is evaporated off under reduced pressure. The residue thus obtained in the form of a white solid is pure (85%).

Physical characteristics:

melting point: 79° C. $^1$H NMR (200 MHz, $CDCl_3$): 1.30 ppm (t; 3H; J=7.16 Hz); 4.22 ppm (q; 2H; J=7.16 Hz); 6.41 ppm (d; 1H; J=15.80 Hz); 7.31 ppm (s; 1H); 7.60 ppm (d; 1H; J=15.80 Hz); 7.72 ppm (s; 1H); 10.16 ppm (bs; 1H).

B/Preparation of ethyl 3-(imidazol-4'-yl) propanoate

The above compound (1.40 g; 8.4 mmol), dissolved in 25 ml of absolute ethanol, is hydrogenated under pressure (2 b) in the presence of 10% palladium on charcoal (Aldrich; 100 mg) for 2 h at room temperature. The suspension is then filtered on a frit; the solvent is evaporated off under reduced pressure. The compound thus obtained in the form of an oil is used as such for the next step (yield: 99%).

Physical characteristics:

$^1$H NMR (200 MHz, $CDCl_3$): 1.21 ppm (t; 2H; J=7.16 Hz); 2.64 ppm (t; 2H; J=7.32 Hz); 2.92 ppm (t; 2H; J=7.32 Hz); 4.10 ppm (q; 2H; J=7.16 Hz); 6.78 ppm (d; 1H; J=1.06 Hz); 7.53 ppm (d; 1H; J=1.06 Hz); 10.49 ppm (bs; 1H). $^{13}$C NMR (50 MHz, $CDCl_3$): 14.35 ppm (q); 22.27 ppm (t); 34.37 ppm (t); 60.88 ppm (t); 117.99 ppm (d); 135.27 ppm (d); 136.06 ppm (s); 174.10 ppm (s).

C/Preparation of ethyl 3-(2'-mercaptoimidazol-4'-yl) propanoate: BXT 52021

Ethyl 3-(imidazol-4'-yl)propanoate (1.30 g; 7.7 mmol) is mixed with sodium bicarbonate (3.90 g; 46.4 mmol) in 20 ml of deionized water and 20 ml of ethyl ether at room temperature. Phenyl chlorothioxoformate (Lancaster; 2.70 ml; 19.5 mmol) is added, with vigorous stirring. The reaction mixture is stirred for 5 h at room temperature. The organic phase is decanted and then washed with a saturated solution of NaCl (2×20 ml) and the solvent is evaporated off under reduced pressure. The residue is taken up in 20 ml of methanol and the resulting solution is treated with triethylamine (Janssen; 3.35 ml; 24.0 mmol) for 16 h at room temperature. The desired product is obtained after evaporation of the solvent and purification by chromatography on a silica column (eluent: AcOEt/cyclohexane 3/2) (yield: 75%).

Physical characteristics:

melting point: 152–154° C. ($CH_3CO_2Et$). $^1$H NMR (200 MHz, $DMSO-d_6$): 1.15 ppm (t; 3H; J=7.26 Hz); 2.58 ppm (m; 4H); 4.04 ppm (q; 2H; J=7.26 Hz); 6.53 ppm (s; 1H); 11.67 ppm (s; 1H); 11.88 ppm (s; 1H). $^{13}$C NMR (50 MHz, $DMSO-d_6$): 14.05 ppm (q); 19.92 ppm (t); 32.16 ppm (t); 60.28 ppm (t); 111.70 ppm (d); 128.21 ppm (s); 160.67 ppm (s); 172.18 ppm (s).

Example 2

Preparation of 3-(2'-mercaptoimidazol-4'-yl) propanoic acid: BXT 52020

Ethyl 3-(2'-mercaptoimidazol-4'-yl)propanoate (200 mg; 1 mmol), dissolved in 10 ml of a THF/water mixture (1/1), is saponified with lithium hydroxide (Aldrich; 84 mg; 2 mmol) at room temperature for 16 h. After neutralization of the reaction medium and evaporation to dryness, the desired product is obtained after recrystallization from absolute ethanol (yield: 93%).

Physical characteristics:

melting point: 204.5–206.5° C. ($H_2O$). $^1$H NMR (200 MHz, $CD_3OD$): 2.57 ppm (m; 2H); 2.73 ppm (m; 2H); 6.56 ppm (s; 1H). $^{13}$C NMR (50 MHz, $CD_3OD$): 21.23 ppm (t); 33.67 ppm (t); 113.51 ppm (d); 131.14 ppm (s); 160.31 ppm (s); 176.24 ppm (t).

Example 3

Preparation of 3-(2'-mercaptoimidazol-4'-yl) propanamide: BXT 52029

Ethyl 3-(2'-mercaptoimidazol-4'-yl)propanoate (320 mg; 145 mmol) is treated with 10 ml of an aqueous solution of ammonium hydroxide (20%) for 20 h at room temperature. The solvent is evaporated off under reduced pressure. The desired product is obtained after purification by liquid chromatography on a silica column (eluent: ethyl acetate/ethanol 3/1) (161 mg; 58%).

Physical characteristics:

melting point: 213–215° C. ($CH_3CH_2OH$). $^1$H NMR (200 MHz, $DMSO-d_6$): 2.29 ppm (t; 2H; J=8.26 Hz); 2.50 ppm (t; 2H; J=8.26 Hz); 6.83 ppm (s; 1H); 7.31 ppm (s; 1H); 11.63 ppm (s; 1H); 11.81 ppm (s; 1H).

Example 4

Preparation of 2-(2'-mercaptoimidazol-4'-yl) ethylamine: BXT 52022

A/Preparation of 2-(2'-mercaptoimidazol-4'-yl)-N$\alpha$-carboxyethylethylamine 2-(Imidazol-4'-yl)-N$\alpha$-carboxyethylethylamine, obtained by the customary procedure, is treated in the same way as in step C of Example 1. The product thus obtained is used as such for the next step.

B/Preparation of 2-(2'-mercaptoimidazol-4'-yl)ethylamine: BXT 52022

The compound obtained above is hydrolyzed by heating under reflux in a concentrated solution of hydrochloric acid for 12 h. The desired product is obtained after recrystallization from methanol.

Physical characteristics:

melting point: 149–251° C. ($H_2O$). $^1$H NMR (200 MHz, $D_2O$): 2.85 ppm (t; 2H; J=6.96 Hz); 3.17 ppm (t; 2H; J=6.96 Hz); 6.77 ppm (s; 1H). MS (EI, 70 eV): 143 (M+, 23%); 114 (24%); 36 (100%).

Example 5

Preparation of 2-(2'-mercaptoimidazol-4'-yl)-N,N-dimethylethyl-amine: BXT 52026

Preparation of 2-(imidazol-4'-yl)-N,N-dimethylethylamine

An aqueous solution of formaldehyde (37%; 111 ml) and 10% palladium on charcoal (0.29 g) are added to a solution of histamine dihydrochloride (Aldrich; 9.1 g; 50 mmol) in 150 ml of deionized water. The mixture is stirred vigorously under hydrogen pressure (5 bar) for 6 h. The catalyst is filtered off and then rinsed with deionized water. The solvent is evaporated off under reduced pressure. The desired product is obtained in the form of an oil (12.7 g), which is used as such for the next step.

Physical characteristics:

$^1$H NMR (200 MHz, D$_2$O): 3.18 ppm (t; 2H; J=7.50 Hz); 3.44 ppm (t; 2H; J=7.50 Hz); 7.33 ppm (s; 1H); 8.60 ppm (s; 1H).

Preparation of 3-(2-mercaptoimidazol-4-yl)-N,N-dimethylethylamine: BXT 52026

The above product, when treated by the same procedure as that described for step C of Example 1, gives the desired compound (34%).

Physical characteristics:

$^1$H NMR (200 MHz, D$_2$O): 2.28 ppm (s; 6H); 2.68 ppm (m; 4H); 6.64 ppm (s; 1H).

Example 6

Preparation of 2'-mercapto-Nα,Nα-dimethyl-L-(+)-histidine: BXT 52040

2'-Mercapto-Nα,Nα-dimethyl-L-(+)-histidine methyl ester is prepared by the following preparative method:

A—Preparation of L-(+)-Nα,Nα-dimethylhistidine methyl ester dihydrochloride

A 37% aqueous solution of formaldehyde (Janssen; 12.29 g; 150 mmol) is added to a solution of L-(+)-histidine methyl ester dihydrochloride (Janssen; 18.16 g; 75 mmol) in 150 ml of deionized water. The mixture is hydrogenated under pressure (7 b) in the presence of 10% palladium on charcoal (Aldrich; 1.0 g) for 5 h at room temperature. The catalyst is filtered off and then rinsed with water; the filtrate is evaporated to dryness under vacuum to give the expected product in the form of an oil (20.3 g), which is used directly in the next step.

Physical characteristics:

$^1$H NMR (200 MHz, D$_2$O): 2.91 ppm (s; 6H); 3.50 ppm (m; 2H); 3.72 ppm (s; 3H); 4.48 ppm (dd; J=5.54–9.04 Hz; 1H); 7.38 ppm (s; 1H); 8.61 ppm (s; 1H).

B—Preparation of L-(+)-2'-mercapto-Nα,Nα-dimethylhistidine methyl ester

L-(+)-Nα,Nα-dimethylhistidine methyl ester dihydrochloride (60.0 g; 222 mmol) is dissolved in 750 nil of deionized water. Solid sodium bicarbonate (Labosi; 130.5 g; 1.55 mmol) is added slowly, followed by 750 ml of THF. Phenyl chlorothioxoformate (Lancaster; 76 ml; 555 mmol) is added over 30 min at a temperature of between 5 and 10° C, with vigorous stirring. The reaction mixture is stirred at room temperature for 260 h. The aqueous phase is decanted and then extracted with methylene chloride (3×150 ml). The organic phases are combined and then evaporated to dryness under vacuum at room temperature. The residue is then purified by chromatography on a silica column using an elution gradient (AcOEt—AcOEt/MeOH=100%-95/5) to give 24.0 g of a pure product. This product (5.0 g) is suspended in 150 ml of methylene chloride and the suspension is then filtered. The residue obtained after evaporation of the solvent from the filtrate gives 4.42 g of an enantiomerically pure product (yield: 42%).

The enantiomeric purity is determined by $^1$H NMR in CDCl$_3$ with 3 mg of sample and 10 mg of Eu(tfc)$_3$.

Physical characteristics:

m.p.: 170–171° C. $^1$H NMR (200 MHz, CDCl$_3$): 2.39 ppm (s; 6H); 2.78 ppm (d; J=7.3 Hz; 2H); 3.38 ppm (t; J=7.30 Hz; 1H); 3.72 ppm (s; 3H); 6.44 ppm (s; 1H); 10.08 ppm (bs; 1H); 10.24 (bs; 1H). $^{13}$C NMR (50 MHz, DMSO): 24.52 ppm (t); 41.03 ppm (q); 51.03 ppm (d); 65.04 ppm (q); 112.74 ppm (d); 126.13 ppm (s); 160.35 ppm (s); 171.17 ppm (s). MS (EI, 70 eV): 229 (M+, 25), 170 (8); 116 (100). α$_D$(c=1.0; MeOH)=+31.2°.

The 2'-mercapto-Nα,Nα-dimethyl-L-(+)-histidine methyl ester thus obtained is then saponified with lithium hydroxide by the customary procedure (yield: 80%).

Physical characteristics:

melting point: 274° C. (dec.). $^1$H NMR (200 MHz, D$_2$O): 2.83 ppm (s; 6H); 3.03 ppm (dd; 1H; J=8.14–15.60 Hz); 3.17 ppm (dd; 1H; J=5.54–15.60 Hz); 3.75 ppm (dd; 1H; J=5.54–8.14 Hz); 6.76 ppm (s; 1H).

Example 7

Preparation of N-2-[3'-(2"-mercaptoimidazol-4"-yl)propanoyloxy]-ethyl-N'-methylpiperazine: BXT 52055

A/Preparation of N-(2-hydroxyethyl)-N'-methylpiperazine:

N-methylpiperazine (10 g; 100 mmol) and 2-chloroethanol (8.05 g; 100 mmol) are stirred at 100° C. for 4 h. The highly viscous reaction medium is supplemented with 250 ml of acetone and the resulting suspension is neutralized with 15 ml of triethylamine. After filtration of the triethylamine hydrochloride, the solvent is evaporated under reduced pressure. The desired compound is obtained after purification by chromatography on an alumina column (Merck®; Aluminum Oxide 90; 63–200 μm, eluent: ethyl acetate) in the form of a colorless oil. Yield: 75%

Physical characteristics:

$^1$H NMR (200 MHz, CDCl$_3$): 2.20 ppm (s; 3H); 2.39 ppm (m; 8H); 2.46 ppm (t; 2H; J=5.5 Hz); 3.41 ppm (sl; 1H); 3.54 ppm (t; 2H; J=5.5 Hz).

B/Preparation of N-2-[3'-(2"-mercaptoimidazol-4"-yl)-propanoyloxy]ethyl-N'-methylpiperazine: BXT 52055

The methyl 3-(2'-mercaptoimidazol-4'-yl)propanoate derivative prepared according to the procedure described in Example 1, (0.35 g; 1.88 mmol) finely ground is placed in N-(2-hydroxyethyl)-N'-methylpiperazine (5.0 g; 35 mmol) in the presence of potassium cyanide (0.12 g; 1.88 mmol). The reaction medium is stirred at 100° C. for 15 h. After distillation of the N-(2-hydroxyethyl)-N'-methylpiperazine excess, under reduced pressure (p=0.5 mm Hg; T°=100° C.), the residue is chromatographed on an alumina column (Merck®; Aluminium Oxide 90; 63–200 μm, eluent: ethyl acetate/methanol 6/1). The desired compound is obtained, after recrystallization from ethyl acetate, with a yield of 80%.

Physical characteristics:

pF: 172–174° C. (ethyl acetate). $^1$H NMR (200 MHz, CD$_3$COCD$_3$+D$_2$O): 2.15 ppm (s; 3H); 2.43 ppm (m; 8H); 2.58 ppm (t; 2H; J=5.6 Hz); 2.69 ppm (m; 4H); 4.16 ppm (t; 2H; J=5.6 Hz); 6.61 ppm (s; 1H). $^{13}$C NMR (50 MHz, D$_2$O): 22.29 ppm; 35.20 ppm; 46.88 ppm; 54.38 ppm; 55.83 ppm; 58.01 ppm; 64.66 ppm; 115.65 ppm; 115.88 ppm; 132.57 ppm; 157.81 ppm; 177.66 ppm. MS (CI; NH$_3$): 299(MH$^+$; 100%); 281 (20%); 267 (85%); 250 (34%); 233 (20%); 187 (15%); 172 (18%); 145 (18%); 127 (30%).

Example 8

Preparation of 2-[3'-(2"-mercaptoimidazol-4"-yl)propanamido]ethanesulfonic acid: BXT 52053

A solution of N,N-dicyclohexylcarbodiimide (0.84 g; 4 mmol) in 10 ml of THF is added dropwise to a solution of 3-(2'-mercaptoimidazol-4'-yl)propanoic acid BXT 52020 (0.69 g; 4 mmol) and N-hydroxysuccinimide (0.46 g; 4 mmol) in 30 ml of anhydrous THF, at 0–5° C. and with stirring. The stirring is maintained for 16 h at this temperature. After evaporation of the solvent under reduced pressure, the solid residue is taken up in 30 ml of anhydrous acetone. The N,N'-dicyclohexylurea is removed by filtration and the filtrate, cooled to 10° C., is supplemented with a solution of taurine (0.5 g; 4 mmol) in 10 ml of deionized water, containing sodium bicarbonate (0.34 g; 4 mmol). The reaction mixture is stirred for 1 h at room temperature. The desired compound is obtained after evaporation of the solvent under reduced pressure and purification by chromatography on a graft silica column (Merck®; RP-8; 40–63 μm) with a water/methanol eluent 9/1. It is recrystallized from a methanol/ethanol mixture (yield: 60%).
Physical characteristics:
m.p.: 210° C. (dec.). $^1$H NMR (200 MHz, $D_2O$): 2.47 ppm (t; 2H; J=7.1 Hz); 2.74 ppm (t; 2H; J=7.1 Hz); 2.96 ppm (t; 2H; J=6.8 Hz); 3.47 ppm (t; 2H; J=6.8 Hz); 6.62 ppm (s; 1H). $^{13}$C NMR (50 MHz, $D_2O$): 23.09 ppm; 37.02 ppm; 37.67 ppm; 52.35 ppm; 115.91 ppm; 116.03 ppm; 132.47 ppm; 157.66 ppm; 177.59 ppm. MS (negative FAB; glycerol): 278 ($M^-$; 100%); 255 (10%); 183 (64%); 124 (14%).

Example 9

Preparation of choline 3-(2'-mercaptoimidazol-4'-yl) propanoate chloride: BXT 52054

A/Preparation of 2-(N,N-dimethylamino)ethyl 3-(2'-mercaptoimidazol-4'-yl)-propanoate:

A solution of ethyl 3-(2'-mercaptoimidazol-4'-yl) propanoate (see Example 1) (1.40 g; 7 mmol) in 120 ml of 2-(N,N-dimethylamino)ethanol is heated in the presence of potassium cyanide (0.75 g; 3.9 mmol) at 80° C. for 4 h. After evaporation of the 2-(N,N-dimethylamino)ethanol under reduced pressure, the desired product is obtained and used as, such for the next step.

B/Preparation of 2-(N,N-dimethylamino)ethyl 3-(1'-tert-butoxycarbonyl-2'-tert-butoxycarbonylthioimidazol-4'-yl) propanoate:

Di-tert-butyl pyrocarbonate (3.3 g; 15 mmol) and triethylamine (5 ml; 36 mmol) as well as 4-dimethylaminopyridine (10 mg) are added to a solution of the above product in 50 ml of methylene chloride. The reaction mixture is stirred at room temperature for 2 h. After addition of 30 ml of water, the organic phase is decanted, dried over magnesium sulfate and filtered. The solvent is evaporated under reduced pressure. The residue thus obtained is purified by chromatography on a silica column (eluent: acetone) to give the desired product which is obtained in the form of a colorless oil.
Overall yield for these 2 steps: 75%
Physical characteristics:
$^1$H NMR (200 MHz, $CDCl_3$): 1.46 ppm (s; 9H); 1.57 ppm (s; 9H); 2.25 ppm (s; 6H); 2.53 ppm (t; 2H; J=5.86 Hz); 2.69 ppm (m; 2H); 2.86 ppm (m; 2H); 4.16 ppm (t; 2H; J=5.86 Hz); 7.33 ppm (s, 1H). $^{13}$C NMR (50 MHz, $CDCl_3$): 28.00 ppm; 28.30 ppm; 33.30 ppm; 45.98 ppm; 58.04 ppm; 62.62 ppm; 86.18 ppm; 87.12 ppm; 119.15 ppm; 135.74 ppm; 142.17 ppm; 147.14 ppm; 165.80 ppm; 173.45 ppm. MS (CI; $NH_3$): 444 ($MH^+$; 100%); 344 (18%).

C/Preparation of choline 3-(1'-tert-butoxycarbonyl-2'-tert-butoxycarbonylthio-imidazol-4'-yl)propanoate iodide:

A solution of 2-(N,N-dimethylamino)ethyl 3-(1'-tert-butoxycarbonyl-2'-tert-butoxycarbonylthioimidazol-4'-yl) propanoate (0.81 g; 1.8 mmol) in 20 ml of THF is treated with methyl iodide (0.6 ml; 9.6 mmol) at room temperature for 2 h. The excess methyl iodide as well as the solvent are evaporated under reduced pressure to give the desired product which is sufficiently pure to be used as such for the next step.
Yield: 100%
Physical characteristics:
$^1$H NMR (200 MHz, $CDCl_3$): 1.44 ppm (s; 9H); 1.56 ppm (s; 9H); 2.73 ppm (m; 2H); 2.86 ppm (m; 2H); 3.48 ppm (s; 9H); 4.06 ppm (m; 2H); 4.55 ppm (m; 2H); 7.37 ppm (s; 1H). $^{13}$C NMR (50 MHz, $CDCl_3$): 23.23 ppm; 27.98 ppm; 28.38 ppm; 33.41 ppm; 55.11 ppm; 58.27 ppm; 65.45 ppm; 86.63 ppm; 87.64 ppm; 119.50 ppm; 135.62 ppm; 141.48 ppm; 146.98 ppm; 165.71 ppm; 172.41 ppm. MS (positive FAB; glycerol): 458 ($M^+$)

D/Preparation of choline 3-(2'-mercaptoimidazol-4'-yl) propanoate chloride:

The above compound (1.07 g, 1.8 mmol) is dissolved in 7.5 ml of methylene chloride and then treated with 7.5 ml of trifluoroacetic acid at room temperature for 2 h. After evaporation of the solvent and the trifluoroacetic acid in excess, under reduced pressure, the residue is purified by chromatography on a silica column (eluent: ethyl acetate-methanol 2/1) to give the desired product.
Yield: 77%
Physical characteristics:
$^1$H NMR (200 MHz, $D_2O$): 2.75 ppm (m; 4H); 3.11 ppm (s; 9H); 3.64 ppm (m; 2H); 4.48 ppm (m; 2H); 6.65 ppm (s; 1H). $^{13}$C NMR (50 MHz, $D_2O$): 22.16 ppm; 35.0,7 ppm; 56.28 ppm; 61.00 ppm; 67.42 ppm; 115.90 ppm; 132.41 ppm; 157.96 ppm; 176.53 ppm. MS (positive FAB; glycerol): 258 ($M^+$)

Example 10

Preparation of carnitine 3-(2'-mercaptoimidazol-4'-yl)propanoate: BXT 52052

Dicyclohexylcarbodiimide (1.1 g; 5.3 mmol) is added to a solution of 3-(2'-mercaptoimidazol-4'-yl)propanoic acid (see Example 2) (0.86 g; 5 mmol) and N-hydroxysuccinimide (0.60 g; 5.2 mmol) in 80 ml of THF. The reaction mixture is stirred at room temperature for 5 h. The solvent is evaporated under reduced pressure to give the mixture of the desired activated ester and N,N'-dicyclohexylurea, which will be used as such for the next step.

Carnitine p-methoxybenzyl ester, prepared from carnitine (0.81 g; 5 mmol) and p-methoxybenzyl chloride (0.79 g; 5 mmol) in 30 ml of anhydrous DMF at 80° C. for 5 h, is mixed with the activated ester of 3-(2'-mercaptoimidazol-4'-yl)propanoic acid prepared above. The reaction mixture is then treated with diisopropylethylamine (1.0 ml; 5.8 mmol) at room temperature for 16 h. The N,N'-dicyclohexylurea is filtered and the solvent is evaporated under reduced pressure. The residue thus obtained is treated with 7.5 ml of 3-mercaptopropanoic acid and 7.5 ml of trifluoroacetic acid at room temperature for 2 h. The trifluoroacetic acid is evaporated under reduced pressure. The residue is taken up in 30 ml of water. The excess 3-mercaptopropanoic acid is extracted with ethyl ether (3×20 ml). The aqueous solution is neutralized with sodium bicarbonate and then freeze-dried. The desired compound is obtained, after purification by chromatography on a graft silica column (Merck®; Diol; 40–63 μm) with an ethyl acetate-methanol eluent 1/3.
Overall yield: 30%
Physical characteristics:
m.p.: 81° C. $^1$H NMR (200 MHz, $D_2O$): 2.39 ppm (dd; 1H; J=7.44-15.53 Hz); 2.53 ppm (dd; 1H; J=5.67-15.53

Hz); 2.75 ppm (m; 4H); 3.06 ppm (s; 9H); 3.53 ppm (d; 1H; J=14.38 Hz); 3.75 ppm (dd; 1H; J=8.46–14.38 Hz); 5.55 ppm (m; 1H); 6.66 ppm (s; 1H). $^{13}$C NMR (50 MHz, $D_2O$): 22.19 ppm; 35.54 ppm; 42.74 ppm; 56.30 ppm; 69.82 ppm; 70.81 ppm; 116.20 ppm; 132.53 ppm; 160.65 ppm; 176.22 ppm; 179.33 ppm. MS (positive FAB; glycerol): 316($MH^+$). $[\alpha]_D$: −36.1° (c=1.0; $H_2O$)

Example 11

Preparation of 2'-mercaptohistidine 2-(trimethylammonium)ethyl ester chloride: BXT 52058

A/Preparation of N,N-bis-tert-butyloxycarbonyl-L-histidine methyl ester:

Sodium carbonate (9.33 g; 88 mmol) is added to a mixture of L-histidine methyl ester dihydrochloride (4.84 g; 20 mmol) in a water-THF mixture (20/40). The di-tert-butyl pyrocarbonate (10 g; 46 mmol) is added while vigorously stirring the mixture obtained. After stirring for 1.5 h at room temperature, the reaction medium is decanted. The aqueous phase is extracted with 50 ml of ethyl acetate. The organic phases from decantation and extraction are combined and the solvent is evaporated under reduced pressure. The crude product is purified by liquid chromatography on a silica column (eluent: ethyl acetate-cyclohexane 1/1).
Yield: 78%
Physical characteristics:
$^1$H NMR (200 MHz, $CDCl_3$): 1.40 ppm (s; 9H); 1.57 ppm (s; 9H); 3.02 ppm (d; 2H; J=5.34 Hz); 3.70 ppm (s; 3H); 4.54 ppm (m; 1H); 5.68 ppm (d; 1H; J=8.06 Hz); 7.11 ppm (d; 1H; J=1.02 Hz); 7.96 ppm (d; 1H, J=1.02 Hz). $^{13}$C NMR (50 MHz, $CDCl_3$): 28.03 ppm; 28.47 ppm; 30.39 ppm; 52.54 ppm; 53.39 ppm; 80.04 ppm; 85.94 ppm; 114.98 ppm; 137.40 ppm; 139.09 ppm; 147.35 ppm; 156.00 ppm; 172.89 ppm.

B/Preparation of 2-mercapto-Nα-tert-butyloxycarbonyl-L-histidine methyl ester:

The desired product is obtained according to a procedure similar to that described in part C of Example 1.
Yield: 32%.
Physical characteristics:
m.p.: 73–75° C. $^1$H NMR (200 MHz, $CDCl_3$): 1.39 ppm (s; 9H); 2.96 ppm (dd; 1H; J=7.60–15.40 Hz); 3.04 ppm (dd; 1H; J=7.60–15.40 Hz); 3.74 ppm (s; 3H); 4.57 ppm (m; 1H); 5.55 ppm (d; 1H; J=6.76 Hz); 6.58 ppm (s; 1H); 11.46 ppm (s; 1H); 11.53 ppm (s; 1H). $^{13}$C NMR (50 MHz, $CDCl_3$): 26.26 ppm, 28.08 ppm; 51.90 ppm; 52.78 ppm; 78.67 ppm; 110.58 ppm; 125.12 ppm; 155.73 ppm; 160.56 ppm; 172.50 ppm.

C/Preparation of the 2-(N,N-dimethylamino)ethyl ester of 3-(1'-tert-butyloxycarbonyl-2'-tert-butyloxycarbonylthioimidazol-4'-yl)-2-tert-butyloxycarbonylaminopropanoic acid:

Potassium cyanide (0.25 g; 1.3 mmol) is added to a solution of the preceding product (760 mg; 1.9 mmol) in 5 ml of 2-(N,N-dimethylamino)ethanol. The reaction mixture is heated at 80° C. for 2 h. The excess 2-(N,N-dimethylamino)ethanol is distilled off. The distillation residue is taken up in 10 ml of methylene chloride. Di-tert-butyl pyrocarbonate (1.09 g; 5 mmol) and triethylamine (0.83 ml; 6 mmol) are added to this solution. The mixture thus obtained is treated with 4-dimethylaminopyridine (5 mg) at room temperature for 1 h. The solvent is evaporated under reduced pressure.

The crude product is purified by liquid chromatography on a silica column (eluent: acetone).
Yield: 38%

Physical characteristics:
$^1$H NMR (200 MHz, $CDCl_3$): 1.35 ppm (s; 9H); 1.41 ppm (s; 9H); 1.52 ppm (s; 9H); 2.18 ppm (s; 6H); 2.48 ppm (t; 2H; J=5.78 Hz); 2.99 ppm (d; 2H; J=5.12 Hz); 4.15 ppm (m; 2H); 4.50 ppm (m; 1H); 5.54 ppm (d; 1H; J=8.06 Hz); 7.34 ppm (s; 1H). $^{13}$C NMR (50 MHz, $CDCl_3$): 27.93 ppm; 28.24 ppm; 28.49 ppm; 30.60 ppm; 45.87 ppm; 53.33 ppm; 57.77 ppm; 63.35 ppm; 80.03 ppm; 86.38 ppm, 87.15 ppm; 120.44 ppm; 136.00 ppm; 138.61 ppm; 146.96 ppm; 155.94 ppm; 165.54 ppm; 172.26 ppm.

D/Preparation of 2'-mercaptohistidine 2-(trimethylammonium)ethyl ester chloride: BXT 52058

A solution of the preceding product (560 mg; 1.0 mmol) in 8 ml of THF is treated with methyl iodide (0.10 ml; 1.6 mmol) at room temperature for 2 h. The excess methyl iodide as well as the solvent are evaporated under reduced pressure. A solution of the residue thus obtained in 10 ml of methylene chloride is percolated with gaseous hydrochloric acid for 1 h at room temperature. The solvent is evaporated under reduced pressure. The product obtained is recrystallized from an ethyl ether-ethanol mixture.
Yield: 80%
Physical characteristics:
m.p.: 141° C. (decomposition). $^1$H NMR (200 MHz, $D_2O$): 3.10 ppm (s; 9H); 3.16 ppm (d; 2H; J=7.50 Hz); 3.65 ppm (m; 2H); 4.40 ppm (t; 1H; J=7.50 Hz); 4.65 ppm (m; 2H); 6.85 ppm (s; 1H).

II/TESTS DEMONSTRATING THE THERAPEUTIC/PHARMACOLOGICAL ACTIVITY

The operating protocols described below make it possible to demonstrate the claimed therapeutic/pharmacological activity of the compounds of the invention of formula (I) given above.

Example 12

Scavenging of Ferrylmyoglobin

The capacity of the molecules of the present invention to scavenge ferrylmyoglobin is demonstrated by a kinetic measurement of the disappearance of ferrylmyoglobin at 590 nm, at pH 7.3 and at 25° C.

The buffer of pH 7.3 is obtained by titrating 50 mM potassium phosphate containing 0.1 mM diethylenetriaminepentaacetic acid (DTPA).

Ferrylmyoglobin is formed by incubating 50 $\mu$M metmyoglobin (purified from horse heart) with 200 $\mu$M hydrogen peroxide ($H_2O_2$) in the above-defined buffer for 4 minutes at 25° C.

The excess $H_2O_2$ is then destroyed by adding about 220 U/ml of catalase to this reaction medium.

Five minutes after the addition of $H_2O_2$, the reaction medium is then supplemented with a molecule according to the present invention (at a final concentration of 25 or 100 $\mu$M) and the kinetics of disappearance of the ferrylmyoglobin is monitored for 5 minutes at an absorbance wavelength of 590 nm.

Figure 1:
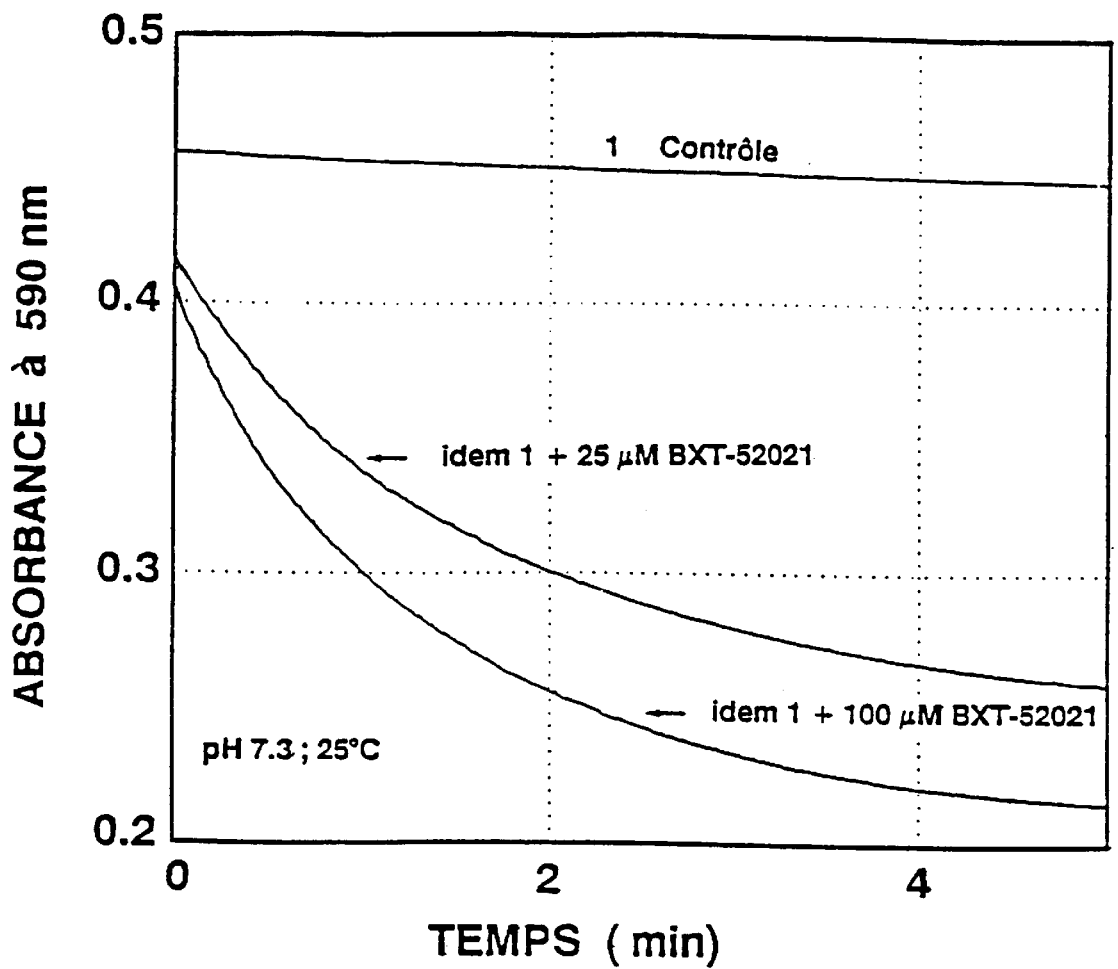
FIG. 1 shows the curves for ferrylmyoglobin reduction, with the time expressed in minutes on the abscissa and the absorbance at 590 nm on the ordinate.

An example of the experimental kinetics obtained in this study is presented in FIG. 1 for the case of BXT 52021.

The effect of the test molecule is measured by determining the percentage of ferrylmyoglobin scavenged after a time of 2 minutes, the value of 100% being determined in the absence of the molecule under the same experimental conditions.

The results obtained are presented in Table 1.

These results show that the molecules described in the present invention scavenge ferrylmyoglobin very effectively.

Example 13

Prevention of the Inactivation of Glutathione Peroxidase by Hypochlorous Acid In a 50 mM potassium phosphate buffer of pH 7.0 containing 0.1 mM DTPA, a quantity of erythrocytic glutathione peroxidase of bovine origin is incubated for 2 minutes at 37° C., at a final concentration of 1.5 U/ml, in the presence of 10 µM hypochlorous acid and in the presence or absence of a molecule described in the present invention (at 25 µM).

After incubation for 2 minutes, 100 µl of this reaction medium are then added to 1.5 ml of 50 mM Tris buffer of pH 7.6 (at 37° C.) containing 0.1 mM DTPA, 0.165 mM β-NADPH, 2.2 mM reduced glutathione and 1.1 U/ml of glutathione disulfide reductase.

Then, after the addition of 50 µl of 6.6 mM t-butyl hydroperoxide, the glutathione peroxidase activity is determined at 37° C. by measuring the decrease in absorbance at 340 nm for 2 minutes.

The results obtained are presented in Table 2. They are expressed as a percentage of the glutathione peroxidase activity determined under the same experimental conditions in the absence of hypochlorous acid and the test molecule.

These results show that the molecules described in the present invention block the inactivation of glutathione peroxidase by hypochlorous acid very effectively.

Example 14

Prevention Of The Inactivation of Glucose-6-Phosphate Dehydrogenase by the System Cu(II)/Ascorbate/$O_2$ In a 50 mM potassium phosphate buffer of pH 7.0, a quantity of glucose-6-phosphate dehydrogenase (purified from *Leuconostoc mesenteroides*) is incubated for 5 minutes at 37° C., at a final concentration of 1.2 U/ml, in the presence of 4.5 µM copper sulfate and 360 µM ascorbate and in the presence or absence of a molecule described in the present invention (at 25 µM).

After incubation for 5 minutes, 20 µl of this reaction medium are then added to 980 µl of 50 mM Tris buffer of pH 7.5 (at 37° C.) containing 0.380 mM β-NADP$^+$, 3.3 mM glucose-6-phosphate and 6.3 mM magnesium chloride.

The glucose-6-phosphate dehydrogenase activity is then determined at 37° C. by measuring, the increase in absorbance at 340 nm for 7 minutes.

The results obtained are presented in Table 3. They are expressed as a percentage of the glucose-6-phosphate dehydrogenase activity determined under the same experimental conditions in the absence of the system Cu(II)/ascorbate/$O_2$ and the test molecule.

These results show that the molecules described in the present invention block the inactivation of glucose 6-phosphate dehydrogenase by the system Cu(II)/ascorbate/$O_2$ very effectively.

Example 15

Prevention of the Degradation of Dna by the System Fe(II) Citrate/$H_2O_2$/Ascorbate In a 50 mM potassium phosphate buffer of pH 7.3, 10 µg/ml of double-stranded DNA (purified from phage lambda) are incubated for 1 hour at 37° C. with 20 µM Fe$^{II}$-citrate complex, 200 µM $H_2O_2$ and 200 µM ascorbate, in the presence or absence of a molecule described in the present invention (at 100 µM).

After this incubation for one hour, 220 U/ml of catalase are then added to the reaction medium and the integrity of the DNA is measured by spectrofluorimetry after the addition of 10 µl of a 5 mM solution of ethidium bromide to the reaction medium (excitation wavelength: 510 nm; emission wavelength: 590 nm).

The effect of the test molecule is measured by determining the percentage of intact DNA, the value of 100% being determined under the same experimental conditions in the absence of the system Fe(II)-citrate/$H_2O_2$/ascorbate and the test molecule.

The results obtained are presented in Table 4.

These results show that the molecules of the present invention prevent the degradation of DNA by the system Fe(II)-citrate/$H_2O_2$/ascorbate very significantly.

Example 16

Inhibition of the Cardiac Necrosis Induced by a Period of Ischemia-Reperfusion: Case of the Compound BXT 52021

The cardioprotective effect of the molecules described in the present invention was demonstrated in an experimental model of perfused isolated heart.

Male Sprague-Dawley rats weighing between 250 and 350 grams are injected intraperitoneally with a solution of sodium heparinate (40 units/100 g). The rats are anesthetized with ether 30 minutes later. The heart is then quickly removed and perfused by Langendorff's method (see 0. LANGENDORFF: Pflügers Arch. Physiol. Mensch. Tiere; (1895); 61; page 291) with electrical stimulation at a frequency of 300/min. The perfusion solution, equilibrated with 95% of oxygen and 5% of carbon dioxide, consists of a modified Krebs-Henseleit buffer (pH 7.4) of the following composition: NaCl 118 mM, KCl 4.7 mM, MgSO$_4$ 1.2 mM, CaCl$_2$ 1 mM, KH$_2$PO$_4$ 1.2 mM, NaHCO$_3$ 25 mM and glucose 11 mM. The whole set-up is thermostatically controlled at 37° C.

The functional state of the heart is monitored by measurement of the following hemodynamic parameters: heart rate, systolic and telediastolic ventricular pressures (the difference between these expressing the developed pressure) and minimal and maximal slopes of the pressure variations as a function of time.

When these hemodynamic parameters have stabilized (i.e. about 30 minutes after the start of perfusion), the heart is subjected to a period of ischemia by stopping the perfusion and the electrical stimulation. Reperfusion is then initiated with resuming the electrical stimulation when the ventricular pressure reaches a maximal value (peak of myocardial contracture due to ischemia).

BXT 52021 is studied in this experimental model by perfusing the heart with a perfusion medium containing 2 µM BXT 52021 for 12 minutes prior to the period of ischemia, and during the reperfusion.

Examination of the results obtained by recording the abovementioned hemodynamic parameters shows that, when the heart is subjected to ischemia-reperfusion, its telediastolic pressure increases and its systolic pressure decreases, whereas the latter is maintained in the presence of BXT 52021.

In addition, the alteration of the myocardial tissue is evaluated by determining the concentration, in the perfusate, of two cytosolic enzymes released into the perfusion medium, namely creatine phosphokinase (CPK) and lactate dehydrogenase (LDH). The concentrations of these two enzymes are expressed in units of enzyme activity per liter of perfusate.

Thus, by measuring these two parameters over time, the degeneration of the myocardial tissue (due to ischemia-reperfusion) or its protection (effect of BXT 52021) are respectively demonstrated by an increase or decrease in the concentrations of CPK and LDH in the perfusate.

Figure 2:
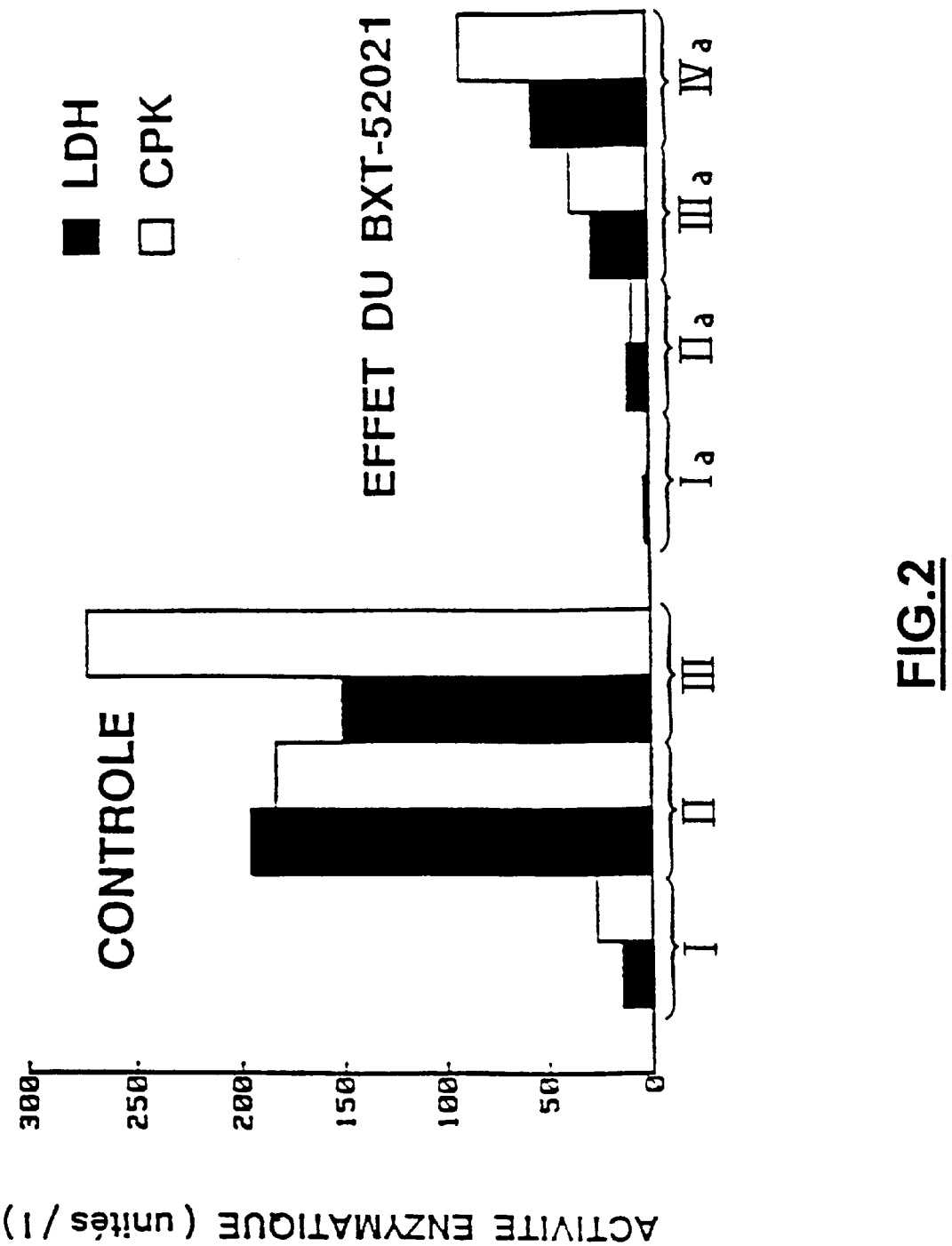
FIG. 2 shows the effect of the compound of the invention, BXT 52021, on the release of lactate dehydrogenase (LDH) and creatine phosphokinase (CPK) in an isolated and perfused rat heart subjected to ischemia-reperfusion, with, on the abscissa, the periods, respectively for the control and the compound of the invention BXT 52021, for LDH in black and CPK in white, and, on the ordinate, the enzyme activity obtained in units/liter. For the control, the numerals I, II and III respectively denote.

The results are presented in FIG. 2. These results show that the molecules according to the present invention make it possible very effectively to protect the myocardial cells from necrosis due to ischemia or to reperfusion.

Example 17

Inhibition of the Cardiac Necrosis Induced by a Period of Ischemia-Reperfusion: Case of The Compound BXT 52053

In the same experimental model as that described in Example 16, the composition of the perfusion solution was modified such that it contains 2.5 mM $CaCl_2$ and 2.4 mM $MgCl_2$ (all else being moreover equal). The effect of BXT 52053 is then compared to that of albumin and L-ergothioneine.

This study is carried out by perfusing the heart with the perfusion solution containing 20 μM BXT 52053, or 600 μM albumin (BSA), or 100 μM L-ergothioneine, during the 12 minutes preceding the period of ischemia, then during the first 30 minutes of post-ischemic reperfusion.

The degradation of the myocardial tissue due to the ischemia and/or reperfusion is evaluated by determining the total quantity of creatine phosphokinase (CPK) released into the perfusate during the period of reperfusion. The results are expressed in milliunits of enzyme activity per milligram of heart and per minute.

The protection of the myocardial tissue is then demonstrated by a decrease in the total quantity of CPK released into the perfusate during the 30 minutes of reperfusion.

The results are presented in FIG. 3.

These results show that albumin or L-ergothioneine have no significant effect whereas the molecules according to the present invention make it possible to protect the cardiac myocytes very effectively and consequently to decrease the extent of cardiac necrosis due to an ischemia and/or to a post-ischemic reperfusion.

Example 18

Improvement in the Recovery of the Developed Pressure of a Heart Subjected to a Period of Ischemia-Reperfusion:

In the same experimental model as that described in Example 17, the study of BXT 52051 and BXT 52052 is carried out by perfusing the heart with the perfusion medium containing 10 μM BXT 52051 or 2 μM BXT 52052 for 12 minutes prior to the period of ischemia, as well as during the reperfusion.

The degradation of the cardiac function is evaluated from the measurement of hemodynamic parameters (systolic and telediastolic ventricular pressures) by determining over time the percentage recovery of the developed pressure (difference between systolic and telediastolic pressure) during the reperfusion, compared to that recorded just before the period of ischemia (stabilized developed pressure).

The results are presented in FIG. 4.

Examination of the results obtained shows that when the heart is subjected to an ischemia-reperfusion, the ventricular developed pressure rises slowly up to a threshold value, whereas it is recovered much more rapidly and reaches a higher value in the presence of BXT 52051 or BXT 52052.

These results show that the molecules according to the present invention make it possible to improve the recovery of the ventricular function of the heart when the latter is subjected to ischemia and then reperfused.

TABLE 1

| Test Molecule | Concentration (μM) | % ferrylmyoglobin scavenged |
|---|---|---|
| BXT 52020 | 25 | 53.1 |
|  | 100 | 71.5 |
| BXT 52021 | 25 | 52.4 |
|  | 100 | 69.5 |
| BXT 52022 | 25 | 36.9 |
|  | 100 | 61.0 |
| BXT 52029 | 25 | 51.1 |
|  | 100 | 70.0 |
| BXT 52030 | 25 | 41.0 |
|  | 100 | 62.3 |

TABLE 2

|  | Concentration (μM) | % glutathione peroxidase activity |
|---|---|---|
| System (1): hypochlorous acid | 10 | 5.2 |
| System (1) + BXT 52020 | 25 | 94.8 |
| System (1) + BXT 52021 | 25 | 94.7 |
| System (1) + BXT 52022 | 25 | 94.4 |
| System (1) + BXT 52029 | 25 | 93.2 |
| System (1) + BXT 52030 | 25 | 106.4 |
| System (1) + BXT 52040 | 25 | 99.1 |

TABLE 3

|  | Concentration (μM) | % glucose-6-phosphate dehydrogenase activity |
|---|---|---|
| System (1): Cu (2+) + ascorbate | 4.5 360 | 10.3 |
| System (1) + BXT 52020 | 25 | 92.3 |
| System (1) + BXT 52021 | 25 | 93.7 |
| System (1) + BXT 52022 | 25 | 94.4 |
| System (1) + BXT 52029 | 25 | 92.3 |
| System (1) + BXT 52030 | 25 | 104.2 |
| System (1) + BXT 52040 | 25 | 104.6 |

TABLE 4

| | Concentration (μM) | % intact DNA |
|---|---|---|
| System (1): Fe(2+)-citrate + acsorbate + $H_2O_2$ | 20 200 200 | 61.8 |
| System (1) + BXT 52020 | 25 | 76.2 |
| System (1) + BXT 52021 | 25 | 78.0 |
| System (1) + BXT 52022 | 25 | 80.2 |
| System (1) + BXT 52029 | 25 | 78.0 |
| System (1) + BXT 52030 | 25 | 74.5 |
| System (1) + BXT 52040 | 25 | 75.3 |

TABLE OF COMPOUNDS DESCRIBED

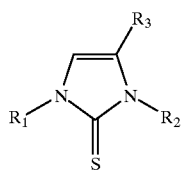

| R1 | R2 | R3 | Example no. | BXT no. |
|---|---|---|---|---|
| H | H | $(CH_2)_2CO_2Et$ | 1 | 52021 |
| H | H | $(CH_2)_2CO_2H$ | 2 | 52020 |
| H | H | $(CH_2)_2CONH_2$ | 3 | 52029 |
| H | H | $(CH_2)_2NH_2$ | 4 | 52022 |
| H | H | $(CH_2)_2N(Me)_2$ | 5 | 52026 |
| H | H | $CH_2CH(COOH)N(Me)_2$ | 6 | 52040 |
| H | H | $(CH_2)_2COO(CH_2)_2$—N⟨piperazine⟩N—$CH_3$ | 7 | 52055 |
| H | H | $(CH_2)_2CONHCH_2SO_3^-$, $Y^+$ | 8 | 52053 |
| H | H | $(CH_2)_2COOCH_2CH_2N+(CH_3)_3X^-$ | 9 | 52054 |
| H | H | $(CH_2)_2COO$-carnitine | 10 | 52052 |
| H | H | $CH_2CH(NH_2)COO(CH_2)_2N^+(CH_3)_3,X^-$ | 11 | 52058 |

What is claimed is:

1. A pharmaceutical, cosmetic or food composition, which comprises, as an active ingredient, at least one 2-mercaptoimidazole compound of general formula (I) below:

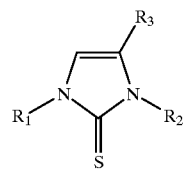

wherein:

$R^1$ is hydrogen, a lower alkyl, an aralkyl group or a substituted aralkyl group;

$R_2$ is hydrogen, a lower alkyl, an aralkyl or a substituted aralkyl, provided that at least one of $R_1$ and $R_2$ is hydrogen;

$R_3$ is —$(CH_2)_nCOR_4$, —$(CH_2)_nN^+(R_5R_6R_7).X^-$ or —$CH_2CH(COR_4)N^+$ $(R_5R_6R_7).X^-$;

$R_4$ is —$OR_8$, —$NHR_5$, -α-amino; —$NHCH_2CH_2SO_3^-$. $Y^+$, —$NHCH_2CH_2CO_2^-$. $Y^+$, —$OCH_2CH_2N^+(CH_3)_3.X^-$;

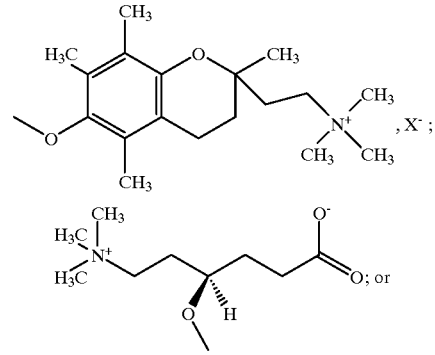

$R_5$ is hydrogen, a lower alkyl, an aralkyl or a substituted aralkyl;

$R_6$ is hydrogen, a lower alkyl, an aralkyl or a substituted aralkyl;

$R_7$ is hydrogen, a lower alkyl, an aralkyl or a substituted aralkyl;

$R_8$ is hydrogen, a lower alkyl, an aralkyl or a substituted aralkyl;

n=1 or 2;

$X^-$ is an anion of an acid acceptable in cosmetics, pharmaceuticals or foodstuffs; and $Y^+$ is a cation of a base acceptable in cosmetics, pharmaceuticals or foodstuffs, excluding L-ergothioneine, in an excipient, carrier or vehicle acceptable in pharmaceuticals, cosmetics or foodstuffs.

2. A process for the manufacture of 2-mercaptoimidazole of general formula (I) below:

wherein:

$R_1$ is hydrogen, a lower alkyl, an aralkyl group or a substituted aralkyl group;

$R_2$ is hydrogen, a lower alkyl, a aralkyl or a substituted aralkyl, provided that at least one of $R_1$ and $R_2$ is hydrogen;

$R_3$ is —$(CH_2)_n(COR_4$, —$(CH_2)_nN^+(R_5R_6R_7)X^-$ or —$CH_2CH(COR_4)N^+$ $(R_5R_6R_7)X^-$;

R₄ is —OR₈, —NHR₅, -α-amino acid, —NHCH₂CH₂SO₃⁻Y⁺, —NHCH₂CH₂CO₂⁻Y⁺, —OCH₂CH₂N⁺(CH₃)₃.X⁻,

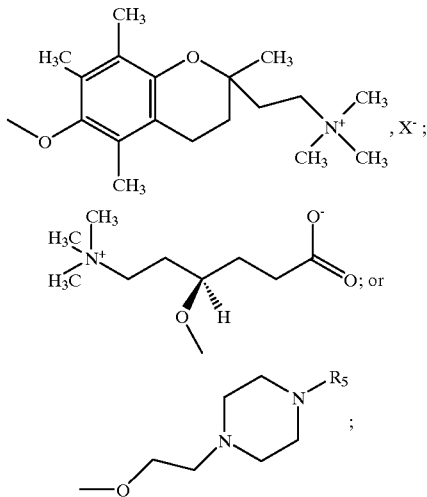

R₅ is hydrogen, a lower alkyl, an aralkyl or a substituted aralkyl;

R₆ is hydrogen, a lower alkyl, an aralkyl or a substituted aralkyl;

R₇ is hydrogen, a lower alkyl, an aralkyl or a substituted aralkyl;

R₈ is hydrogen, a lower alkyl, an aralkyl or a substituted aralkyl;

n=1 or 2;

X⁻ is an anion of an acid acceptable in cosmetics, pharmaceuticals or foodstuffs; and Y⁺ is a cation of a base acceptable in cosmetics, pharmaceuticals or foodstuffs which comprises the steps of:

a) preparing or using an optionally protected imidazole compound substituted in the 4(or 5) -position;

b) treating this imidazole compound with an alkyl, alkenyl or aryl halothionoformiate in a basic medium in a polar solvent;

c) and then;

i—for the preparation of compounds of formula (I) given above in which R₃ is as defined above, with the proviso that R₅, R₆ and R₇ are not all simultaneously other than hydrogen, hydrolyzing in a basic medium or in an acid medium in the presence of a carbonium ion scavenger; or ii—for the preparation of the compounds of formula (I) given in which R₅, R₆ and R₇ are not all simultaneously other than hydrogen, protecting the sulfur-containing substituent and then converting the protected compound to a trialkylammonium compound and hydrolyzing in a basic medium or in an acid medium in the presence of a carbonium ion scavenger.

3. The process as claimed in claim 2 wherein the above mentioned carbonium ion scavenger is a mercaptan selected from the group consisting of an alkyl or aryl mercaptan and β-mercaptopropanoic acid.

4. The process as claimed in claim 2, wherein the above mentioned base is selected from the group consisting of sodium bicarbonate, an amine or an alkylamine, diethylamine and triethylamine.

5. The process as claimed in claim 2, wherein the above mentioned polar solvent is selected from the group consisting of an ether solvent ethyl ether and tetrahydrofuran, or an alcohol.

6. The process as claimed in claim 2, wherein the above mentioned basic hydrolysis is performed with an inorganic base selected from the croup consisting of sodium hydroxide and lithium hydroxide, or an organic base selected from the group consisting of an amine, an alkylamine, diethylamine and triethylamine, in solution in a polar solvent comprising a water/alcohol mixture.

7. The process as claimed in claim 2, wherein the acid hydrolysis is performed with a concentrated solution of strong acid at a pH below 2, in the presence of a carbonium ion scavenger.

8. The process as claimed in claim 2, wherein the above mentioned sulfur-containing substituents are protected by means of a haloformate selected from the group consisting of an alkyl phenyl haloformate, and ethyl or phenyl chloroformate, and the conversion to a trialkylammonium compound is effected by means of an alkylating agent selected from the group consisting of an alkyl halide or sulfate, methyl iodide and dimethylsulfate.

9. The process as claimed in claim 2, wherein an optically active final compound is prepared using an optically active starting compound, which is hydrolyzed with a concentrated acid solution at a pH below 2 and in the presence of a carbonium ion scavenger.

10. A 2-mercaptoimidazole compound substituted in the 4 or 5 position of the general formula (I) below:

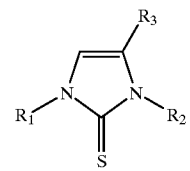

wherein:

R¹ is hydrogen, a lower alkyl, an aralkyl group or a substituted aralkyl group;

R₂ is hydrogen, a lower alkyl an aralkyl or a substituted aralkyl, provided that at least one of R₁ and R₂ is hydrogen;

R₃ is —(CH₂)ₙCOR₄, —(CH₂)ₙN⁺(R₅R₆R₇).X⁻ or —CH₂CH(COR₄)N⁺(R₅R₆R₇).X⁻;

R is —OR, —NHR₅, -α-amino acid; —NHCH₂CH₂SO₃⁻.Y⁺, —NHCH₂CH₂CO₂⁻. Y⁺, —OCH₂CH₂N⁺(CH₃)₃.X⁻;

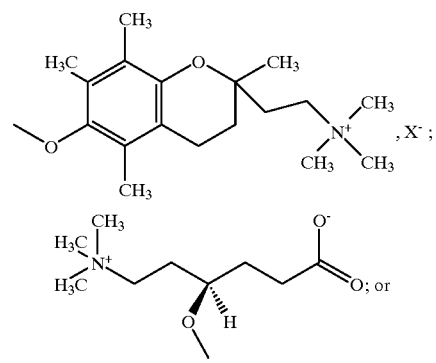

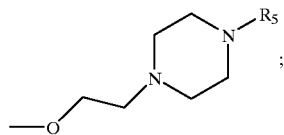

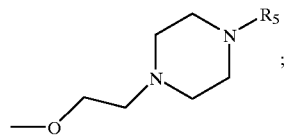

$R_5$ is hydrogen, a lower alkyl, an aralkyl or a substituted aralkyl;

$R_6$ is hydrogen, a lower alkyl, an aralkyl or a substituted aralkyl;

$R_7$ is hydrogen, a lower alkyl, and aralkyl or a substituted aralkyl;

$R_8$ is hydrogen, a lower alkyl, an aralkyl or a substituted aralkyl;

$X^-$ is an anion or an acid acceptable in cosmetics, pharmaceuticals or foodstuffs; and $Y^+$ is a cation of a base acceptable in cosmetics, pharmaceuticals or foodstuffs, and n=2, with the proviso that:

a) if $R_4$=—$OR_8$ or —$NHR_5$, then $R_1$ and $R_2$ cannot simultaneously be hydrogen, b) if $R_3$=—$CH_2CH(COR_4)N^+(R_5R_6R_7).X^-$ and $R_4$=OH, then $R_5$, $R_6$ and $R_7$ cannot simultaneously be a methyl group:

if $R_3$=—$(CH_2)_2N^+(R_5R_6R_7).X^-$, then $R_5$, $R_{66}$ and $R_7$ cannot simultaneously be hydrogen.

11. An antioxidant of the formula (I) below:

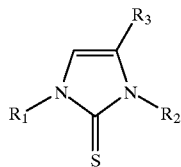

wherein:

$R_1$ is hydrogen, a lower alkyl, an aralkyl group or a substituted aralkyl group;

$R_2$ is hydrogen, a lower alkyl, an aralkyl or a substituted aralkyl, provided that at least one of $R_1$ and $R_2$ is hydrogen;

$R_3$ is —$(CH_2)_nCOR_4$, —$(CH_2)_nN^+(R_5R_6R_7).X^-$ or —$CH_2CH(COR_4)N^+(R_5R_6R_7).X^-$;

$R_4$ is —$OR_8$, —$NHR_5$, -α-amino acid, —$NHCH_2CH_2SO_3^-.Y^+$, —$NHCH_2CH_3CO_2^-.Y^+$, —$OCH_2CH_2N^+(CH_3)_3.X^-$,

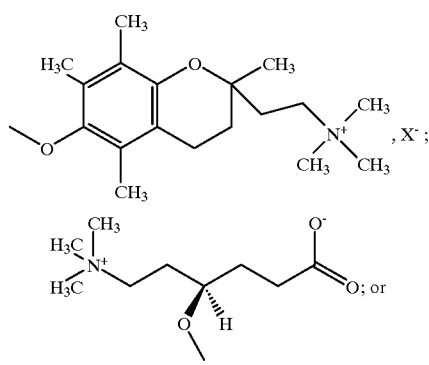

$R_5$ is hydrogen, a lower alkyl, an aralkyl or a substituted aralkyl;

$R_6$ is hydrogen, a lower alkyl, an aralkyl or a substituted aralkyl;

$R_7$ is hydrogen, a lower alkyl, an aralkyl or a substituted aralkyl;

$R_8$ is hydrogen, a lower alkyl, an aralkyl or a substituted aralkyl;

n=1 or 2;

$X^-$ is an anion of an acid acceptable in cosmetics, pharmaceuticals or foodstuffs; and $Y^+$ is a cation of a base acceptable in cosmetics, pharmaceuticals or foodstuffs, with the proviso that:

a) if $R_4$=—$OR_8$ or —$NHR_5$, then $R_1$ and $R_2$ cannot simultaneously be hydrogen, b) if $R_3$=—$CH_2CH(COR_4)N^+(R_5R_6R_7).X^{31}$ and $R_4$=OH, then $R_5$, $R_6$ and $R_7$ cannot simultaneously be a methyl group;

c) if $R_3$=—$(CH_2)_2N^+(R_5R_6R_7).X^-$, then $R_5$, $R_6$ and $R_7$ cannot simultaneously be hydrogen.

12. A pharmaceutical composition with antioxidant activity, comprising, as an active ingredient, at least one antioxidant as claimed in claim 11.

13. A method for the treatment of a pathological condition involving an oxidative stress associated with an overproduction of oxidizing free radicals or an intracellular decompartmentalization of the pool of certain transition metals selected from iron, copper and manganese, comprising the step of administering an antioxidatively effective amount of an antioxidant as claimed in claim 11.

14. The method as claimed in claim 13 wherein administration of said antioxidant is for treating tissue degeneration induced by ischemia and/or post-ischemic reperfusion; for treating myocardial infarction; for treating post-ischemic cardiac arrhythmia which is the source of ventricular fibrillation; for treating tissue degeneration, associated with an overproduction of free radicals; for treatment of intoxication by xenobiotics or pathological conditions associated with oxidation stress on erythrocytes, for protecting against irradiation by ionizing X-rays, gamma rays or UV rays; and for protecting, in preserving media, grafts in organ transplants.

15. A cosmetic composition with antioxidant activity, for protecting against UV rays, comprising an antioxidatively effective amount of an antioxidant as claimed in claim 11.

16. A food composition with antioxidant activity, comprising an antyloxidatively effective amount of an antioxidant as claimed in claim 11.

17. The composition according to claim 12 wherein the antioxidant is included in an amount of between 0.1 to 5 percent by weight based on a total weight of the pharmaceutical composition.

18. The composition according to claim 12 wherein the antioxidant is included in an amount between 0.1 to 1.0 percent by weight, based on a total weight of the pharmaceutical composition.

19. The composition according to claim 15 wherein the antioxidant is included in an amount of between 0.1 to 5 percent by weight based on a total weight of the cosmetic composition.

20. The composition according to claim 15 wherein the antioxidant is included in an amount of between 0.1 to 1.0 percent by weight based on a total weight of the cosmetic composition.

21. The composition according to claim 16 wherein the antioxidant is included in an amount of between 0.1 to 5 percent by weight based on a total weight of the food composition.

22. The composition according to claim 16 where the antioxidant is included in amount of between 0.1 to 1.0 percent by weight based on a total weight of the food composition.

23. The composition according to claim 12 wherein the pharmaceutical composition is prepared in the form of a unit dose which comprises from 1 to 500 mg of the antioxidant.

24. The composition according to claim 23, further comprising a pharmaceutically acceptable excipient, vehicle or carrier.

25. The method as claimed in claim 14 wherein said tissue degeneration is selected from edema, necroses and fibroses.

26. The method as claimed in claim 14 wherein said xenobiotics are selected from the group consisting of paraquat, diquat, anthracyclines and nitrofurans.

27. The method as claimed in claim 14 wherein said pathological conditions associated with oxidation stress on erythrocytes are selected from the group consisting of sickle cell anemia, thalassemia, glucose-6-phosphate dehydrogenase deficiency and malaria.

28. The method as claimed in claim 14 wherein said grafts are selected from the group consisting of heart, liver, kidney and lung.

29. A pharmaceutical composition comprising a pharmaceutically effective amount of ethyl 3-(2'-mercaptoimidazol-4'-yl)propanoate in a pharmaceutically acceptable excipient.

30. A pharmaceutical composition comprising a pharmaceutically effective amount of 3-(2'-mercaptoimidazol-4'-yl) propanoic acid in a pharmaceutically acceptable excipient.

31. A pharmaceutical composition comprising a pharmaceutically effective amount of 3-(2'-mercaptoimidazol-4'-yl) propanamide in a pharmaceutically acceptable excipient.

32. A pharmaceutical composition comprising a pharmaceutically effective amount of 2-(2'-mercaptoimidazol-4'-yl) ethylamine in a pharmaceutically acceptable excipient.

33. A pharmaceutical composition comprising a pharmaceutically effective amount of 2-(2'-mercaptoimidazol-4'-yl)-N,N-dimethylethylamine in a pharmaceutically acceptable excipient.

34. A pharmaceutical composition comprising a pharmaceutically effective amount of 2'-mercapto-N$\alpha$,N$\alpha$-dimethyl-L-(+)-histidine in a pharmaceutically acceptable excipient.

35. A pharmaceutical composition comprising a pharmaceutically effective amount of N-2-[3'-(2"-mercaptoimidazol-4"-yl)propanoyloxy]-ethyl-N'-methylpiperazine in a pharmaceutically acceptable excipient.

36. A pharmaceutical composition comprising a pharmaceutically effective amount of 2-[3'-(2"-mercaptoimidazol-4"-yl)-propanamido]-ethanesulfonic acid in a pharmaceutically acceptable excipient.

37. A pharmaceutical composition comprising a pharmaceutically effective amount of choline 3-(2'-mercaptoimidazol-4'-yl)propanoate chloride in a pharmaceutically acceptable excipient.

38. A pharmaceutical composition comprising a pharmaceutically effective amount of carnitine 3-(2'-mercaptoimidazol-4'-yl)propanoate in a pharmaceutically acceptable excipient.

39. A pharmaceutical composition comprising a pharmaceutically effective amount of 2'-mercaptohistidine 2-(trimethylammonium)ethyl ester chloride in a pharmaceutically acceptable excipient.

* * * * *